United States Patent
Chen et al.

[11] Patent Number: 6,102,909
[45] Date of Patent: Aug. 15, 2000

[54] SCISSORLIKE ELECTROSURGICAL CUTTING INSTRUMENT

[75] Inventors: Chao Chen, Edison; Emil Richard Skula, Wayne; Donald W. Regula, Belle Mead, all of N.J.

[73] Assignee: Ethicon, Inc., Somerville, N.J.

[21] Appl. No.: 08/918,875

[22] Filed: Aug. 26, 1997

[51] Int. Cl.$^7$ .................................................. A61B 18/14
[52] U.S. Cl. ................... 606/45; 606/46; 606/48; 606/49; 606/50; 606/51; 606/52; 606/170; 606/174; 606/208
[58] Field of Search ................ 606/45, 46, 48–52, 606/170, 174, 208

[56] References Cited

U.S. PATENT DOCUMENTS

| | | |
|---|---|---|
| 3,754,516 | 8/1973 | VanGompel . |
| 3,989,033 | 11/1976 | Halpern et al. . |
| 4,058,126 | 11/1977 | Leveen . |
| 4,248,231 | 2/1981 | Herczog et al. . |
| 4,711,240 | 12/1987 | Goldwasser et al. ............... 606/174 |
| 5,085,659 | 2/1992 | Rydell ................................... 606/50 |
| 5,176,695 | 1/1993 | Dulebohn . |
| 5,190,541 | 3/1993 | Abele et al. ......................... 606/50 |
| 5,330,471 | 7/1994 | Eggers . |
| 5,352,222 | 10/1994 | Rydell . |
| 5,361,583 | 11/1994 | Huitema ............................... 606/51 |
| 5,431,674 | 7/1995 | Basile et al. . |
| 5,556,407 | 9/1996 | Wurster et al. . |
| 5,702,390 | 12/1997 | Austin et al. ....................... 606/50 |
| 5,827,281 | 10/1998 | Levin .................................. 606/52 |

FOREIGN PATENT DOCUMENTS

| | | |
|---|---|---|
| 0092170 | 10/1983 | European Pat. Off. ............. 606/51 |
| 0 717 966 A1 | 6/1996 | European Pat. Off. . |
| WO 96/27338 | 9/1996 | WIPO . |

OTHER PUBLICATIONS

N.P. Chironis (1965) Mechanisms, Linkages, and Mechanical Controls McGraw–Hill Book Company: 72–75.

*Primary Examiner*—Lee Cohen
*Attorney, Agent, or Firm*—Scully, Scott, Murphy & Presser

[57] ABSTRACT

Open surgery and endoscopic versions of an electrosurgical cutting instrument incorporating a unique cutting arrangement for opening and closing the cutting edge parallel to an anvil surface resulting in a simultaneous cutting of a linear section of tissue, large vessels, or a group of vessels. Simultaneous with the cutting, the instrument further being capable of either a monopolar or bipolar cauterization of tissue. Also disclosed herein, are methods for use of the various electrosurgical cutting instruments.

41 Claims, 16 Drawing Sheets

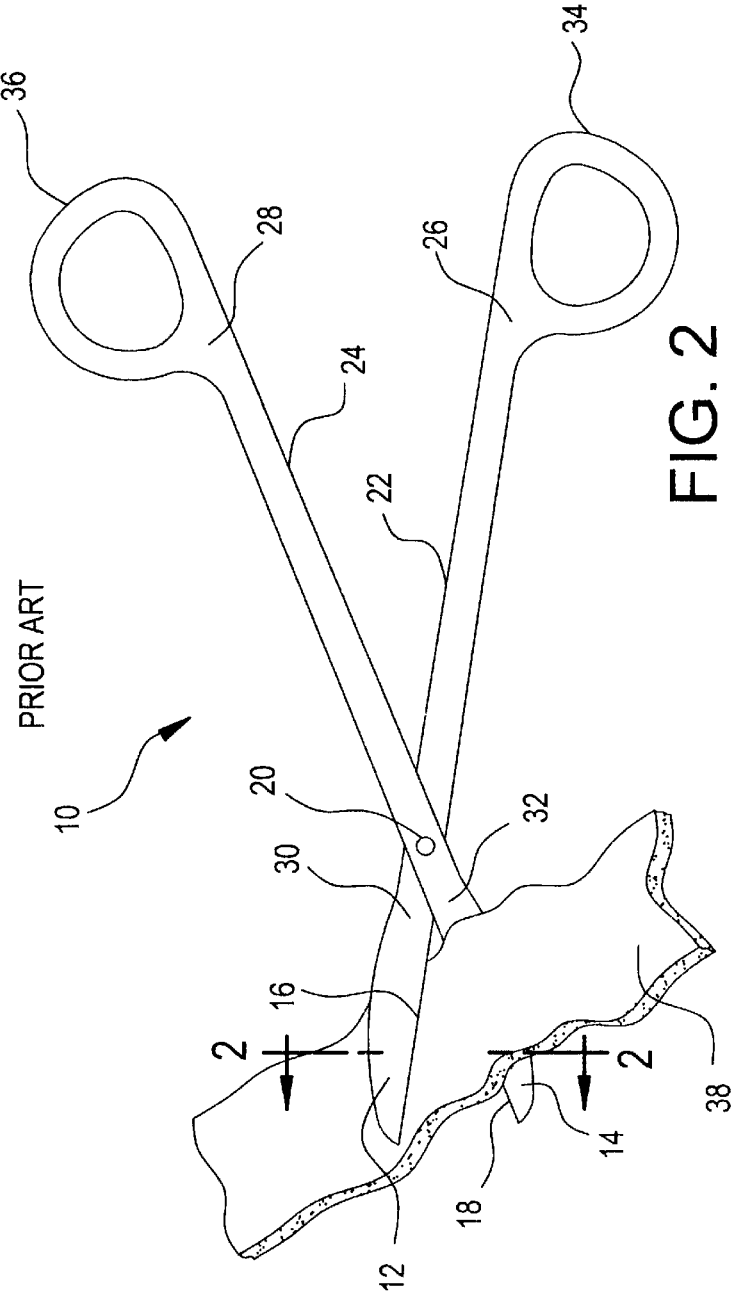
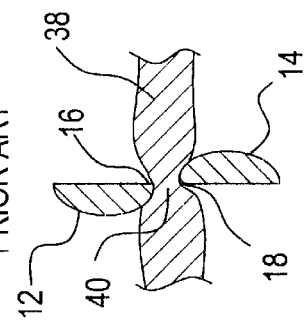

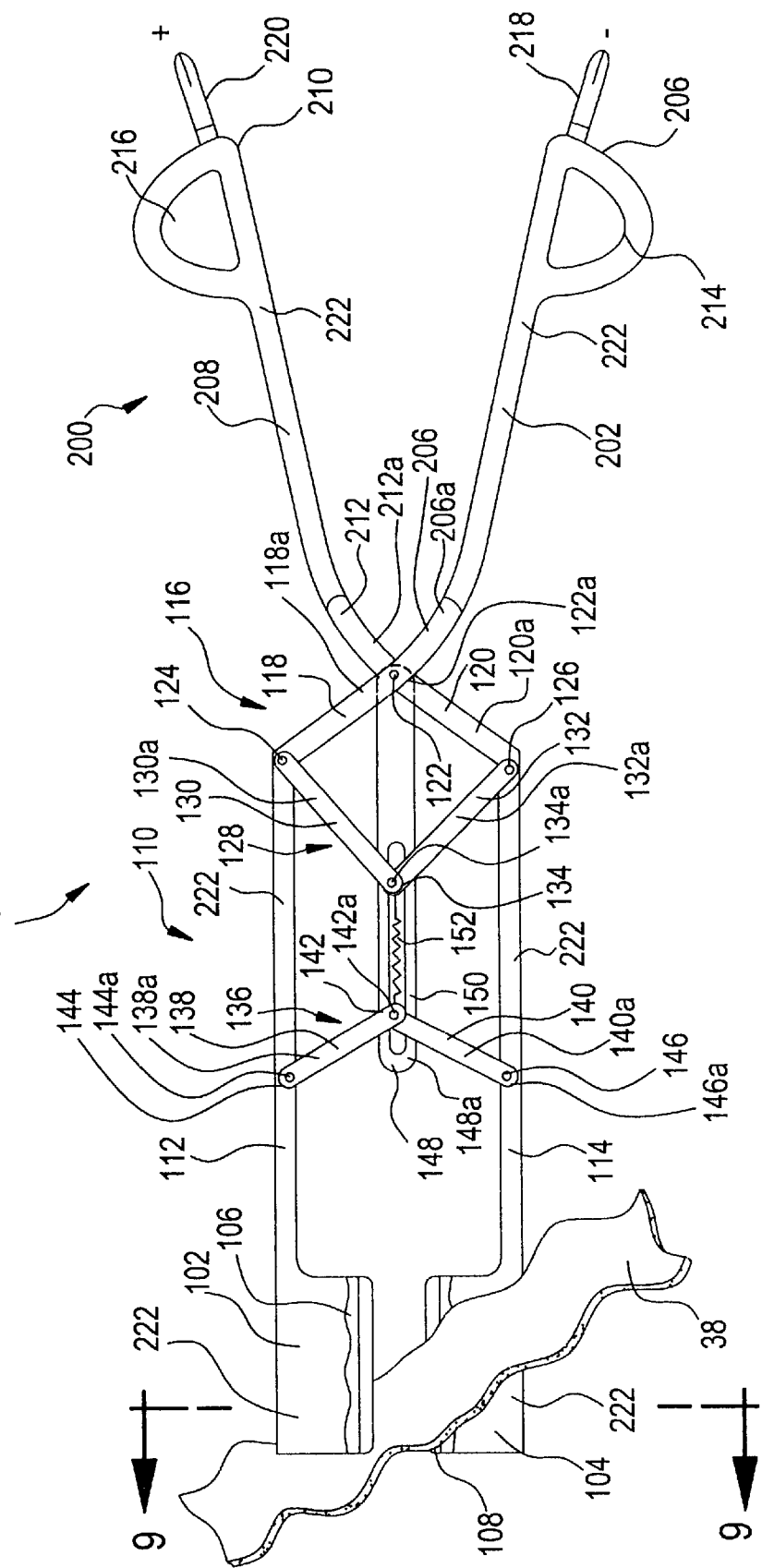

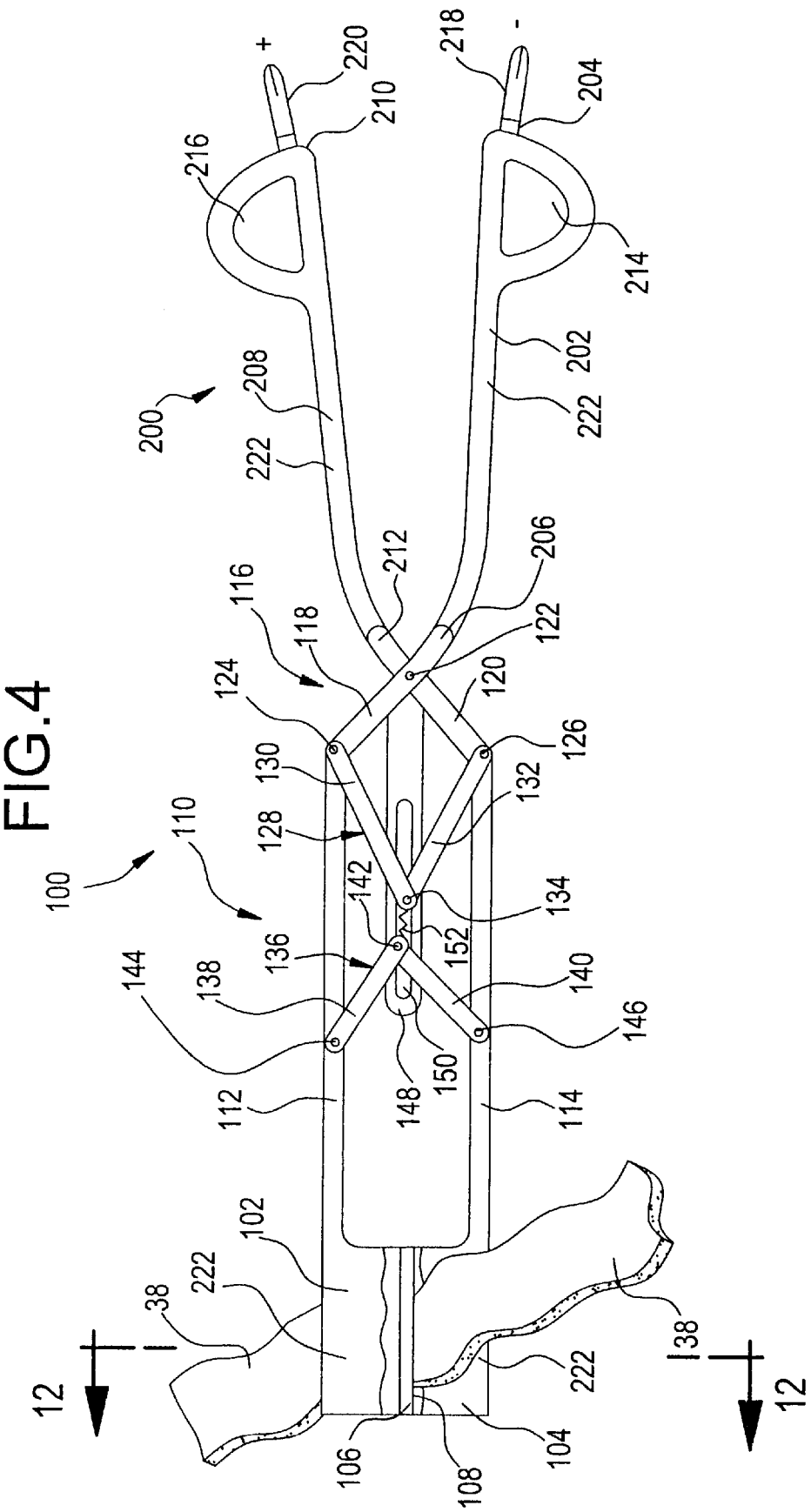

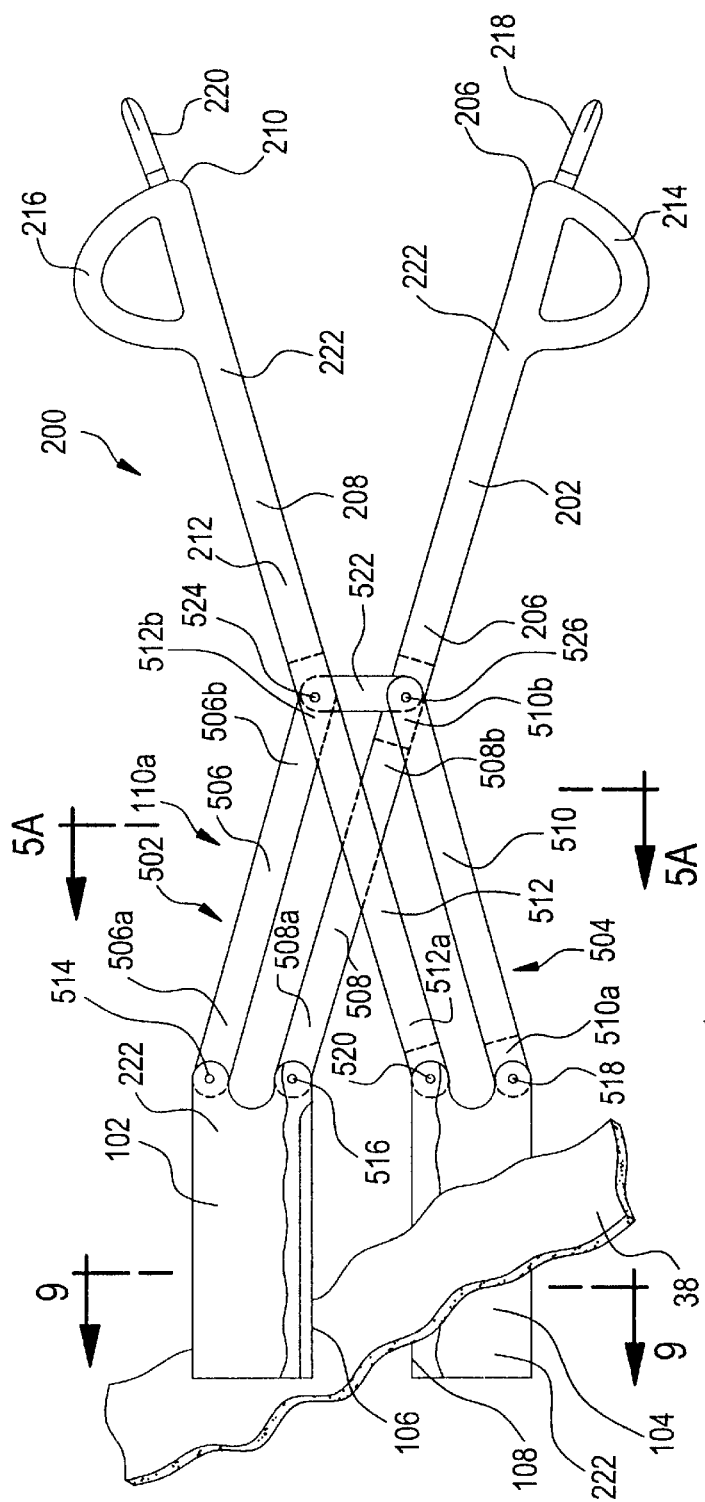
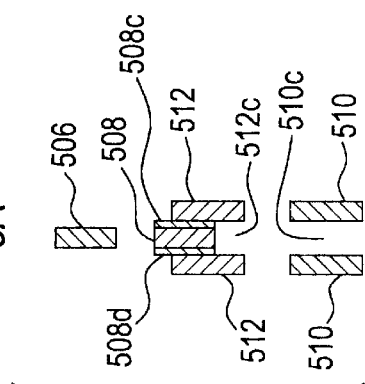

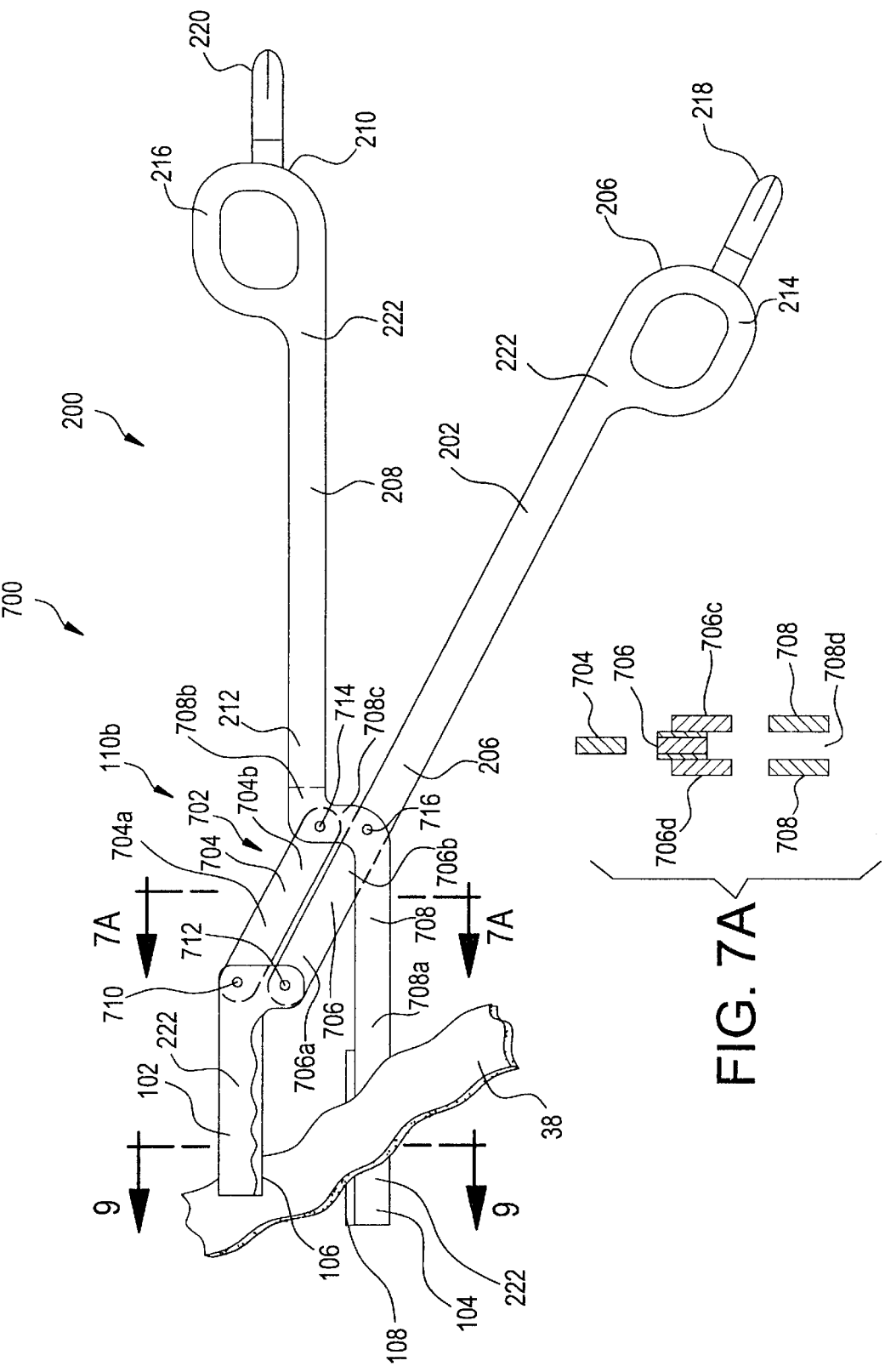

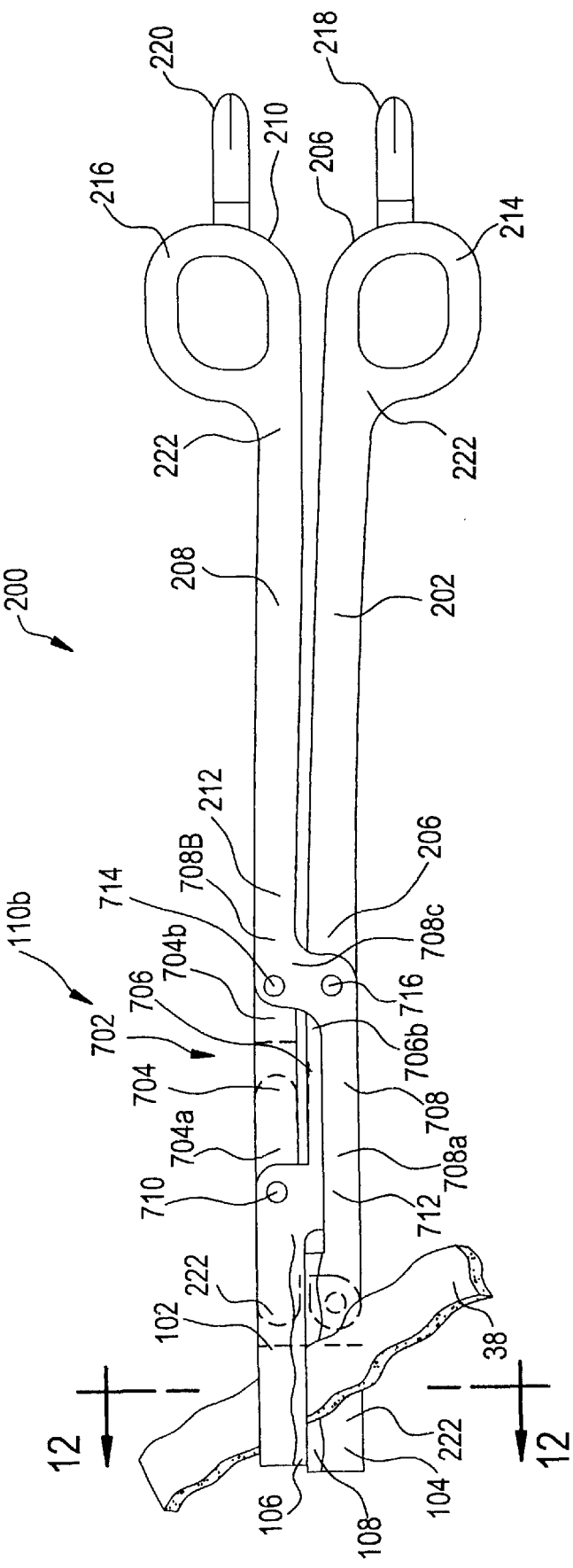

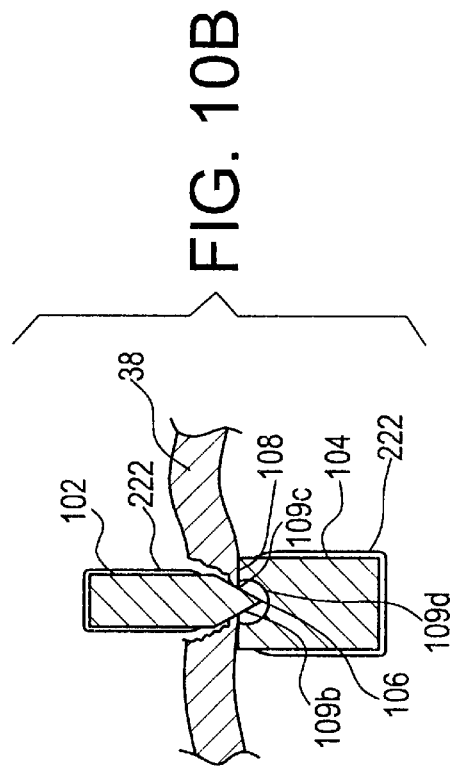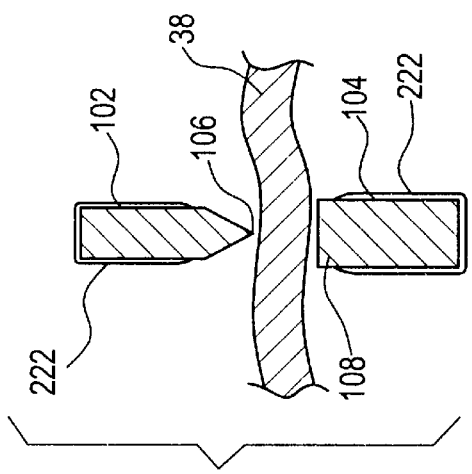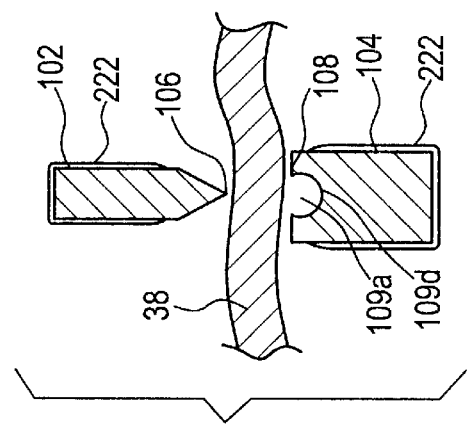

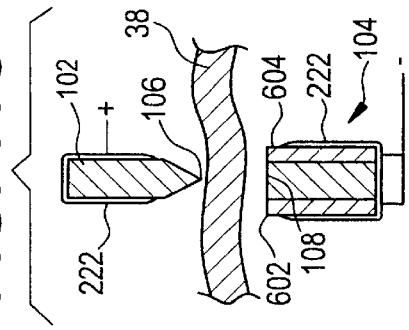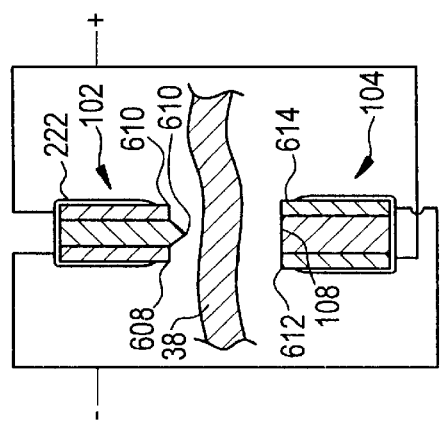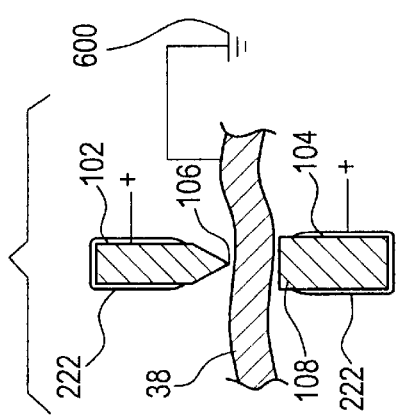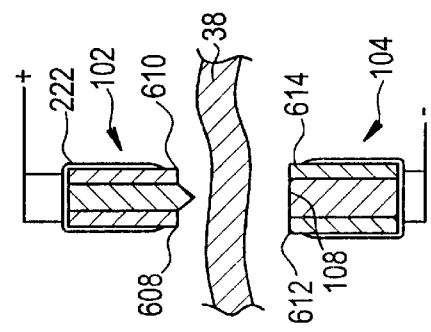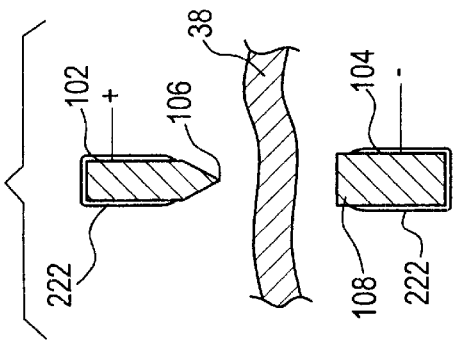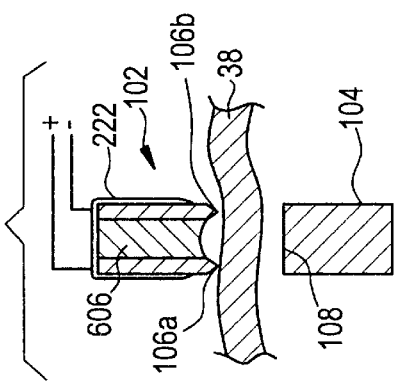

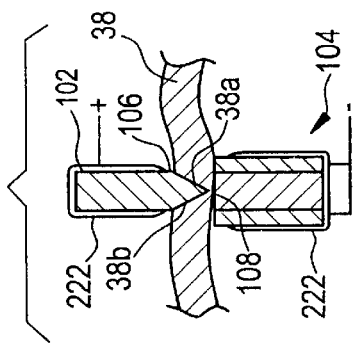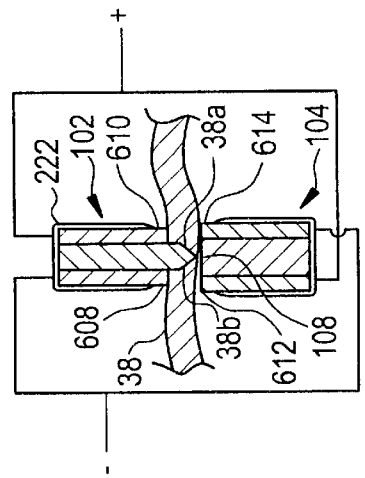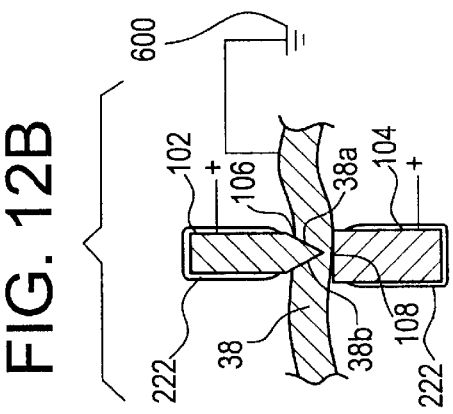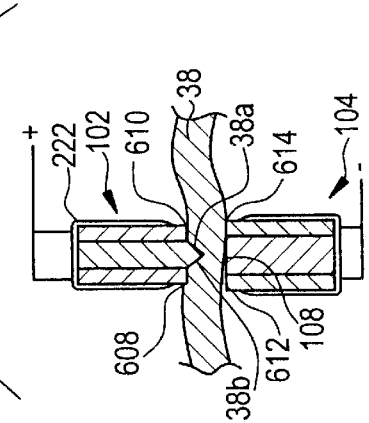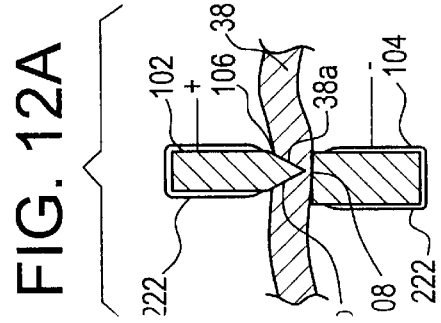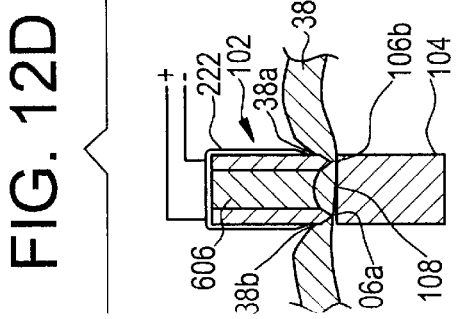

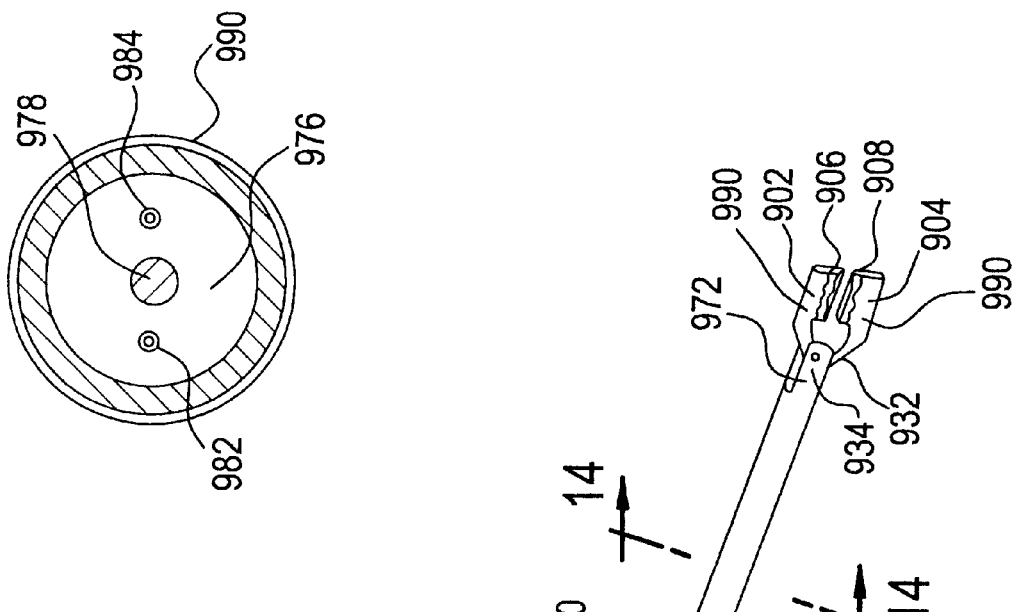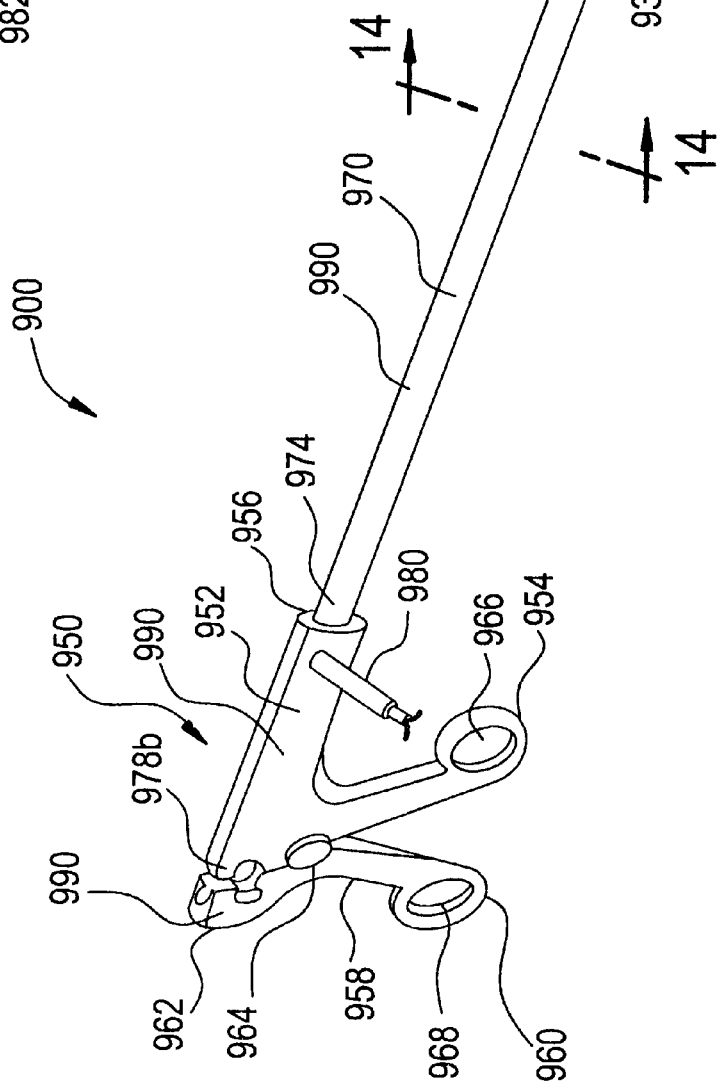

SCISSORLIKE ELECTROSURGICAL CUTTING INSTRUMENT

BACKGROUND OF THE INVENTION

1. Field of the Invention

The field of art to which this invention relates is surgical instruments, in particular, electrosurgical cutting instruments.

2. Description of the Related Art

Surgical instruments which mechanically cut tissue are well known in the surgical arts. A surgical scissor for use in open surgical procedures is illustrated in FIG. 1 and referred to generally by reference numeral 10. The scissor has two opposing blades 12,14, each with a cutting edge 16,18. The blades pivot about a pin, rivet, or screw 20. The scissors 10 further having first and second elongated members 22,24, each member having a proximal end 26,28 and a distal end 30,32. Finger loops 34,36 are provided at the proximal ends 26,28 of the first and second elongated members 22,24. The blades 12,14 are disposed at the distal ends 30,32 of the elongated members.

Referring now to FIG. 2, the blades 12,14 are shown cutting a piece of tissue 38. As can be seen, the cutting edges 16,18, when closed upon the tissue 38, at a time just prior to cutting, causes a region of tissue 40 to tear, resulting in trauma to the tissue.

The cutting of tissue during a surgical procedure results in bleeding. Controlling bleeding during surgery accounts for a major portion of the time involved in surgery. In particular, bleeding that occurs when tissue is incised or severed can obscure the surgeon's vision, prolong the operation, and adversely effect the precision of cutting. Blood loss from surgical cutting may require blood infusion, thereby increasing the risk of harm to the patient.

Electrosurgical instruments have been developed for reducing bleeding by cauterizing tissue and coagulating blood. These instruments include both monopolar and bipolar devices in which radio frequency (RF) energy is used to provide the heat necessary for cauterization and coagulation. Monopolar devices are typically used in conjunction with a grounding pad wherein one pole of an electrosurgical generator is mounted to the instrument and one pole is mounted to the grounding pad. Electrical current travels from the instrument through the patient's body to the grounding pad. Bipolar instruments are typically connected to both poles of the electrosurgical generator. Current flow is typically limited to tissue adjacent to the working end of the bipolar instrument.

Furthermore, these instruments can be of a reusable type (the instrument is cleaned and disinfected or sterilized before each use) or a disposable type (disposed of after each use). Each of these types can be provided in different sizes, shapes, and configurations so as to be suitable for either endoscopic or open surgery.

In "open" surgical procedures, the surgeon gains access to work inside the body by cutting large incisions through the body wall, then stretching the overlying tissue apart to provide visibility and room to manipulate his hands and instruments. Because of the relatively large working area provided in open surgical procedures, the instruments used can be larger. They typically have conventional scissors handles with finger loops and a pivot point about which the handles pivot to actuate the working end.

In endoscopic surgical procedures, a trocar provides a puncture wound in the body wall. The trocar is removed leaving a hollow tube providing access to the body cavity. A miniature television camera is inserted through the trocar tube to provide a video image of the inside of the body cavity. Specially designed surgical instruments are then inserted through other small trocar tubes to perform the surgery. Surgical instruments of this type typically have a long tubular body designed to pass through the trocar tubes. The working end, connected to the distal end of the tubular body must likewise pass through the trocar tubes and are therefore typically small in cross section. Typically, a scissors-like actuating means or a pistol grip actuating means is disposed on the proximal end of the tubular body to remotely actuate the working end. The actuating means is typically connected to the working end by a mechanical linkage.

More recently, electrosurgical cutting devices have been developed which combine mechanical cutting with electrosurgical cauterization and cutting. Examples of these devices include electrosurgical scissors.

U.S. Pat. No. 5,330,471 discloses bipolar electrosurgical scissors having electrically insulated cutting edges. The cutting edges provide for simultaneous hemostasis and mechanical cutting of tissue. U.S. Pat. No. 5,352,222 discloses bipolar electrosurgical scissors. The scissors have blade supports with blades mounted thereto and separated by a layer of insulation. U.S. Pat. No. 4,248,231 discloses an electrosurgical scalpel wherein an instrument is disclosed having an insulated blade and electrode mounted thereto.

Although the electrosurgical cutting devices of the prior art are useful and effective, there are several deficiencies associated with their use. In particular, as the scissor blades rotate in a scissors-like manner, the mechanical cutting of tissue occurs in a limited area at a point immediately adjacent to the closure point of the cutting edges. Additional disadvantages of conventional electrosurgical scissors include:

a. They are not very useful for large cutting and dissecting;

b. The scissor-like motion which requires a sliding point of contact between blades causes the blades to wear, increasing the trauma to the cut tissue caused by the dull blades; and c. Scissor-like instruments are very difficult to manufacture, requiring complex surface contours, strict dimensional tolerances, and precise blade adjustment.

Accordingly, there is a need in the art for an improved electrosurgical cutting instrument which is capable of simultaneous cutting and cauterization of a linear section of tissue.

SUMMARY OF THE INVENTION

Therefore, it is an object of the present invention to provide an electrosurgical cutting instrument capable of simultaneously cutting and cauterizing a linear section of tissue.

It is a further object of the present invention to provide an electrosurgical cutting instrument which provides for improved coagulation of blood and cauterization of tissue.

It is yet another object of the present invention to provide an electrosurgical cutting instrument for use with large vessels.

It is yet another object of the present invention to provide an electrosurgical cutting instrument for use with a group of vessels.

It is yet another object of the present invention to provide an electrosurgical cutting instrument which reduces the amount of trauma to tissue during cutting.

It is yet another object of the present invention to provide an electrosurgical cutting instrument in which the cutting edges are less prone to wear.

It is still yet another object of the present invention to provide an electrosurgical cutting instrument which is simpler and less expensive to produce.

Accordingly, an electrosurgical cutting instrument is disclosed. The device has a first member having at least one conductive cutting edge. The device further has a second member having a conductive anvil surface opposing the cutting edge. A means for maintaining the cutting edge parallel to the anvil surface is provided in which at least one of the members moves relative to the other between an open and a closed position such that, when in a closed position, the cutting edge is in contact with the anvil surface. The instrument further has an electrode for providing electrical energy to cauterize tissue. Also provided, is an actuation means for opening and closing the first and second members.

In a second embodiment of the present invention the device has a first member having at least one cutting edge. The device further has a second member having an anvil surface opposing the cutting edge. A means for maintaining the cutting edge substantially parallel to the anvil surface is provided in which at least one of the members moves relative to the other between an open and a closed position such that, when in a closed position, the cutting edge is in contact with the anvil surface. At least two electrodes of opposite polarity are provided for supplying electrical energy to cauterize tissue. An isolating means electrically isolates the first member from the second member. Also provided, is an actuation means for opening and closing the first and second members.

In a variation of the second embodiment of the present invention the cutting edge comprises an electrode. The second member has two electrodes of the same polarity, but of an opposite polarity to that of the cutting edge. The anvil surface having a non-conductive material for electrically isolating one electrode of the second member from the other electrode of the second member.

In another variation of the second embodiment of the present invention, the anvil surface of the second member is non-conductive. The first member having two cutting edges, each cutting edge comprises an electrode, one electrode being of opposite polarity to the other. The first member further having a non-conductive insulating layer disposed between the cutting edge electrodes for electrically isolating one cutting edge electrode from the other.

In a third embodiment of the present invention, the device has a first member having at least two conductive electrodes and at least one non-conductive cutting edge. The non-conductive cutting edge electrically isolates the electrodes of the first member from each other. A second member is provided having at least two conductive electrodes and at least one non-conductive anvil surface. The non-conductive anvil surface electrically isolates the electrodes of the second member from each other. The device further having a means for maintaining the cutting edge substantially parallel to the anvil surface in which at least one of the first and second members moves relative to the other member between an open and closed position such that the cutting edge comes into substantial contact with the anvil surface when the members are in their closed position. Also provided is an isolating means for electrically isolating the first member from the second member and an actuation means for opening and closing the first and second members.

In a variation of the third embodiment of the present invention the first member has two electrodes of the same polarity. The second member also has two electrodes of the same polarity. The electrodes of the second member oppose the electrodes of the first member. The electrodes of the first and second members are arranged such that each electrode is opposed by an electrode of the opposite polarity.

In another variation of the third embodiment of the present invention, the first member has two electrodes, each electrode being of a different polarity. The second member also has two electrodes, opposing the electrodes of the first member, each electrode being of a different polarity. The electrodes of the first and second members are arranged such that each electrode is opposed by an electrode of an opposite polarity.

In a fourth embodiment of the present invention, the device has a first member having at least one conductive cutting edge and a second member having at least one conductive anvil surface opposing each cutting edge. Also provided is a means for maintaining each cutting edge substantially parallel to each opposing anvil surface in which at least one of the first and second members moves relative to the other member between an open and closed position such that each cutting edge comes into substantial contact with each opposing anvil surface when the members are in their closed position. The device also has at least two pairs of electrodes, each pair of electrodes being of the same polarity and arranged such that the individual electrodes of at least one pair oppose each other. Lastly, an isolating means for electrically isolating the first member from the second member and an actuation means for opening and closing the first and second members are provided.

In a variation of the fourth embodiment of the present invention, the first member has first and second cutting edges, each cutting edge being an electrode of opposite polarity. The first member further having a non-conductive material disposed between cutting edges for electrically isolating one cutting edge from the other. The second member has first and second anvil surfaces where each anvil surface opposes each cutting edge of the first member and being an electrode of opposite polarity. The second member further having a non-conductive material disposed between anvil surfaces for electrically isolating one anvil surface from the other. Lastly, the electrodes of the first and second members are arranged such that electrodes of like polarities oppose each other thereby forming two pairs of opposing electrodes where the individual electrodes within each pair have the same polarity and the pairs have opposite polarity to each other.

In another variation of the fourth embodiment of the present invention the first member has a cutting edge, the cutting edge being an electrode having a polarity. The second member has one anvil surface opposing the cutting edge of the first member. The anvil surface being an electrode of the same polarity as the cutting edge of the first member thereby forming a first pair of electrodes with the same polarity. The second member further having a second pair of electrodes of the same polarity, but opposite in polarity to the first pair of electrodes. The second member further having non-conductive material disposed between the anvil surface and the individual electrodes of the second pair of electrodes for electrically isolating the individual electrodes of the second pair of electrodes from each other and from the anvil surface.

In a variation of any of the preceding embodiments of the present invention, and variations thereof, both members move relative to each other.

In a further variation of any of the preceding embodiments of the present invention, and variations thereof, the means for maintaining a parallel cutting edge is provided by a mechanical linkage.

In a further variation of any of the preceding embodiments of the present invention, and variations thereof, a biasing means is provided for biasing the first and second members in an open or closed position.

In a further variation of any of the preceding embodiments of the present invention, and variations thereof, the anvil surface further has a recessed portion for acceptance of the cutting edge when the first and second members are in their closed position.

In a further variation of any of the preceding embodiments, and variations thereof, the instrument is sized, shaped, and configured to be suitable for open surgical procedures.

In a further variation of any of the preceding embodiments, and variations thereof, the instrument is sized, shaped, and configured to be suitable for endoscopic surgical procedures.

Another aspect of the present invention are methods of using the various embodiments, and variations thereof, of the present invention.

BRIEF DESCRIPTION OF THE DRAWINGS

These and other features, aspects, and advantages of the instruments and methods of the present invention will become better understood with regard to the following description, appended claims, and accompanying drawings where:

FIG. 1 illustrates a typical cutting instrument of the prior art, the scissor blades thereof being shown in an open position about a piece of tissue;

FIG. 2 illustrates a sectional view taken along line 2—2 in FIG. 1;

FIG. 3 illustrates a front view of a first embodiment of the present invention useful in open surgical procedures, the first and second members thereof being shown in an open position about a piece of tissue;

FIG. 4 illustrates the embodiment of FIG. 3 with the first and second members being closed upon a piece of tissue;

FIG. 5 illustrates a front view of a second embodiment of the present invention useful in open surgical procedures, the first and second members thereof being shown in an open position about a piece of tissue;

FIG. 5A illustrates a sectional view taken along line 5A—5A in FIG. 5;

FIG. 7 illustrates a front view of a third embodiment of the present invention useful in open surgical procedures, the first and second members thereof being shown in an open position about a piece of tissue;

FIG. 7A illustrates a sectional view taken along line 7A—7A in FIG. 7;

FIG. 8 illustrates the embodiment of FIG. 7 with the first and second members being closed upon a piece of tissue;

FIG. 9 illustrates a sectional view taken along line 9—9 in any one of the embodiments illustrated in FIGS. 3, 5, or 7;

FIGS. 10A and 10B illustrate a preferred embodiment of the anvil surface of the second member, the first and second members thereof being shown in an open position in FIG. 10A and in a closed position in FIG. 10B;

FIGS. 11A–11H illustrate sectional views of various operating end configurations of the present invention as taken along line 9—9 in any one of the embodiments illustrated in FIGS. 3, 5, or 7;

FIGS. 12A–12H illustrate the various blade configurations of FIGS. 11A–11H with the first and second members being closed upon a vessel as taken along line 12—12 in FIGS. 4, 6, or 8;

FIG. 13 illustrates an isometric view of an endoscopic embodiment of the present invention, the first and second members thereof being shown in an open position;

FIG. 14 illustrates a sectional view as taken along the line 14—14 in FIG. 13;

DETAILED DESCRIPTION OF THE PREFERRED EMBODIMENTS

Figure 6:
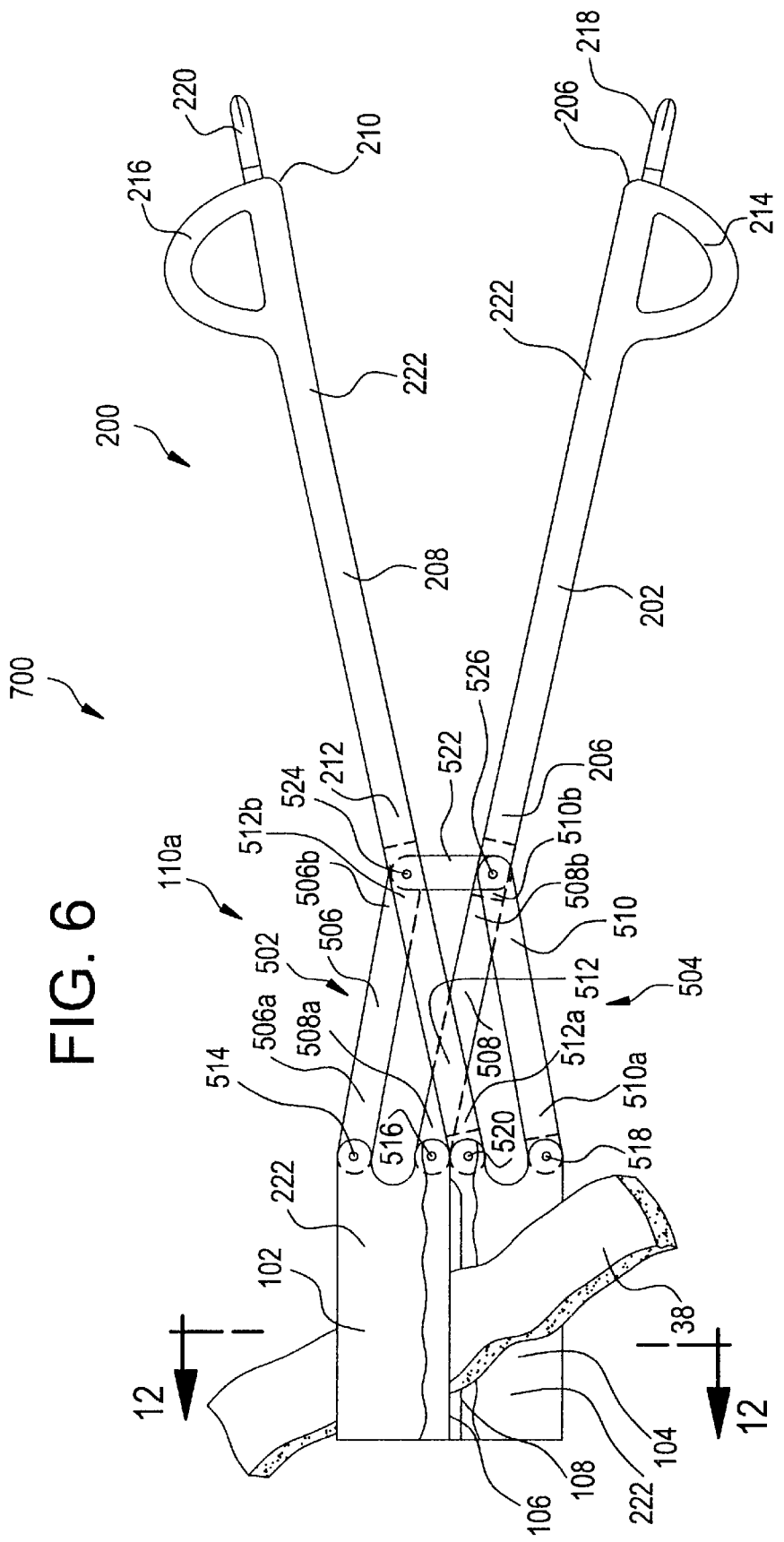
FIG. 6 illustrates the embodiment of FIG. 5 with the first and second members being closed upon a piece of tissue.

Referring now in detail to FIGS. 3, 4, and 9 there is illustrated a bipolar open surgery variation of the inventive electrosurgical cutting instrument 100 which includes a first member 102 and a second member 104. The first member 102 has at least one cutting edge 106. The second member 104 has an anvil surface 108 opposing the cutting edge 106 of the first member 102. In the preferred embodiment, the first member 102 and second member 104 move relative to each other. However, one of the members can also be made to move, while the other member is stationary.

It should be understood that the cutting edge 106 and anvil surface 108 are shown to be linear, resulting in a linear profile cut. However, the cutting edge 106 and opposing anvil surface 108 can be curved, or have curved sections to provide a desired profile cut.

Referring now to FIGS. 10A and 10B, a preferred anvil surface 108 is shown having a recessed portion 109a. The recessed portion 109a is shaped such that the cutting edge 106 can pass into the recessed portion 109a and contact the edges of the recessed portion 109b,109c without the cutting edge 106 contacting the bottom of the recessed portion 109d. Because there is no contact of the cutting edge 106 with any other surface, the cutting edge 106 remains sharper longer.

Referring back to FIGS. 3, 4, and 9 a means for maintaining the cutting edge 106 parallel with the anvil surface 108 in which both the first member 102 and second member 104 move relative to each other between an open and closed position is supplied by a mechanical linkage, generally referred to as reference numeral 110. The mechanical linkage 110, of which any straight-line or parallel movement linkage can be employed, has a first rigid member 112 which may be formed as an integral part of the first member 102. Likewise, the mechanical linkage 110 has a second rigid member 114 which may be formed as an integral part of the second member 104. The first rigid member 112, and second rigid member 114 are substantially parallel to each other and of the same length. Each rigid member has a cantilevered end 124, and 126 respectively.

A first linkage 116 is supplied having two link elements of equal length, referred to by reference numerals 118 and 120. Each link having a first and second end, the first ends are pivotally connected together at 122, the second ends are pivotally connected to the first and second rigid members 112,114, at the cantilevered ends 124 and 126 respectively.

A second linkage 128 also has two link elements of equal length 130, 132, and are of equal length to the link elements 118, 120 of the first linkage 116. Again, each link having a first and second end, the first ends are pivotally connected together at 134, the second ends are pivotally connected to the first and second rigid members 112,114, and the link elements 118, 120 of the first linkage 116, at 124 and 126 respectively. A third linkage 136 also has two link elements of equal length 138, 140, and are of equal length to the link elements 118, 120 of the first linkage 116 and the link elements 130,132 of the second linkage 128. Again, each link having a first and second end, the first ends are pivotally connected together at 142, the second ends are pivotally connected to the first and second rigid members at 144 and 146 respectively. Points 144 and 146, except for being opposite each other, are arbitrarily chosen along the length of the first and second rigid members 112, 114.

A fixed member 148 is pivotally connected at the first ends 122 of the link elements 118,120 of the first linkage 116. The second ends 134, 142 of the second and third linkages 128, 136 are slidably retained in a slot 150 in the fixed member 148. A spring 152 is disposed within the slot 150 and connected between points 134 and 142 to bias the first member 102 and second member 104 in their open position.

All pivoting points used on the instrument are accomplished by means well known in the art, such as with pins, screws, or rivets. They generally are fabricated from a durable conductive material, preferably stainless steel, which is coated with an insulating material, preferably aluminum oxide. However, the pins, rivets, or screws can also be fabricated from a high strength polymer which is either glass or ceramic filled. The pins, screws, or rivets can also be fabricated entirely from a ceramic, and furthermore the ceramic can be impregnated with a polymer to increase its lubricity.

Actuating means, referred to generally as reference numeral 200, is supplied for opening and closing the first and second members 102,104 between their open and closed positions in which a first handle lever 202 having a proximal end 204 and a distal end 206 is provided. Also provided, is a second handle lever 208 having a proximal end 210 and a distal end 212. The distal end 206 of the first handle lever 202 is integral with, a link element 120 of the first linkage 116. Likewise, the distal end 212 of the second handle lever 208 is integral with, the other link element 118 of the first linkage 116. The handle levers 202, 208 pivot about the first ends 122 of the first linkage 116. Finger loops 214 and 216 are disposed on the proximal ends 204,210 of the first and second handle levers 202,208 respectively.

To actuate the instrument, a user inserts his or her fingers into the finger loops 214,216 and squeezes them together or spreads them apart, to actuate the first and second members 102,104 between their open and closed positions.

Starting from an open position, the user squeezes his fingers together which causes the link elements 118,120 to pivot about point 122. Link elements 130,132 of the second linkage 128 will likewise pivot about points 134, 124, and 126. The parallelogram formed by the first and second linkages 116,128 will flatten out since points 124 and 126 would move towards each other. Point 134 will rotate and translate within slot 150 to keep the parallelogram symmetrical about the fixed member 148.

Simultaneously, the third linkage 136 will pivot about points 144 and 146, and point 142 will rotate and translate within slot 150 forming angles with respect to the fixed member 148 that are equal to the angles the second linkage 128 forms relative to the fixed member 148. Because of this link arrangement, the first and second rigid members 112, 114, and the first and second members 102,104 connected therewith are constrained to move parallel to each other and toward each other until the cutting edge 106 contacts the anvil surface 108, as shown in FIG. 4.

To open the first and second members 102,104, the above described motion is reversed, with the spring 152, aiding the user by exerting a biasing force outward towards points 134 and 142, biasing the first and second members 102,104 into their open position.

In a bipolar arrangement, as shown schematically in its simplest form in FIG. 11A, at least two electrodes, of opposite polarity are provided for supplying electrical energy for cauterization of tissue 38. In the preferred embodiment the first member 102 serves as a first electrode of a certain polarity, and the second member 104 serves as the other electrode of the opposite polarity. As can be seen in FIG. 12A, when the cutting edge 106 is closed upon the anvil surface 108 and electrical energy supplied, the tissue 38 is severed and its cut edges 38a,38b cauterized. Any blood in the vicinity of the cut edges 38a,38b is coagulated.

Referring back to FIGS. 3 and 4, the electrical energy is supplied to the first member 102 by an electrosurgical generator (not shown) via a power cord (not shown). The power cord electrically connects to a first connector port 218 located on the proximal end 204 of the first handle lever 202. Electrical energy of the opposite polarity is supplied to the second member 104 which is electrically connected to a second connector port 220 located on the proximal end 210 of the second handle lever 208.

Electrical energy from the first connector port 218 flows through the first handle lever 202, through the link element 118 of the first linkage 116 to which it is connected, through the first rigid member 112, to the first member 102 to which it is connected, all of which are made of a conductive material, preferably stainless steel. Likewise, electrical energy of an opposite polarity from the second connector port 220 flows through the second handle lever 208, through the link element 120 of the first linkage 116 to which it is connected, through the second rigid member 114, to the second member 104 to which it is connected, all of which are also made of a conductive material, preferably stainless steel.

To isolate the two electrical paths, an isolating means is provided to electrically isolate the first member from the second member. In the preferred embodiment, as shown in FIGS. 3 and 4, the isolating means is accomplished by disposing insulating coatings of aluminum oxide to link elements 118, 120, 130, 132, 138, and 140, referred to as 118a, 120a, 130a, 132a, 138a, and 140a respectively. A coating of aluminum oxide is also disposed on the fixed member 148, referred to as 148a, to the distal end portions 206,212 of the first and second handle levers 202,208, referred to as 206a and 212a, and on pivot points 122, 134, 140, 142, 144, and 146, referred to as 122a, 134a, 140a, 142a, 144, and 146a.

The aluminum oxide is applied by a plasma deposition process. The thickness of the aluminum oxide coating is between 0.003 and 0.010 inches thick, preferably, between 0.005 and 0.007 inches thick to withstand a voltage of 1,500 volts.

Alternatively, the isolating means can be accomplished by fabrication of the link elements 130, 132, 138, 140 and fixed member 148 from an insulating material, such as a high strength polymer or ceramic. A layer of aluminum oxide must still be disposed on the distal end portions 206,212 of the first and second handle levers 202,208, referred to as 206a and 212a, and on the pivot pin 122, referred to as 122a, in order to electrically isolate the two conductive paths which cross at pivot point 122.

Lastly, an insulating means is provided for preventing electrical conduction from portions of the instrument other than the electrodes. Preferably, the insulating means comprises a nylon coating 222 secured to all portions of the instrument where electrical conduction is not wanted. This most likely includes all portions of the instrument except the cutting edge 106, anvil surface 108, connector posts 218, 220, and portions of the electrodes closest to where they meet when the first and second members 102,104 are in their closed position (if the electrodes are not the cutting edge 106 or the anvil surface 108). This insulating coating serves to protect the user from electrical shock and burning, and also the patient from electrical shock and burning in areas other than those intended.

The open surgery electrosurgical cutting instrument 100 of the present invention can also be configured in a monopolar version, as shown in FIGS. 11B and 12B. In a monopolar version, only one polarity is provided, the other polarity being provided by the patient's body, by which current flows back to the electrosurgical generator. In this configuration, both the cutting edge 106 and the anvil surface 108 are electrodes of the same polarity, a grounding plate (shown schematically as ground 600) attached to the patient and to the electrosurgical generator allows current to flow from the instrument through the patient and back to the generator. Electrical current is supplied to the instrument in a similar fashion, except that only one connector port, fixed to the proximal end of one of the handle levers, is necessary. In this configuration an isolating means is not necessary since there is only one current path through the instrument.

Additionally, other bipolar arrangements are possible, some of which are shown in FIGS. 11C through 11H. These variations are preferred over the simple bipolar arrangement shown in FIG. 11A as will be explained below.

FIG. 11C shows a schematic diagram of a bipolar arrangement of electrodes where the cutting edge 106 of the first member 102 comprises an electrode, as is the arrangement previously discussed above, and shown in FIG. 11A. However, first and second electrodes 602,604 are provided on the second member 104, both electrodes 602,604 being of the same polarity as each other but of an opposite polarity from the cutting edge 106. The anvil surface 108, disposed between the first electrode 602 and the second electrode 604, is a non-conductive material and serves as an isolating layer, for electrically isolating the first electrode 602 from the second electrode 604. The anvil surface 108 is preferably made of a non-conductive insulating material which is also durable enough to withstand the pressure applied by the cutting edge 106, such as aluminum oxide.

As shown in FIG. 12C, when in a closed position, electrical energy flows through the tissue 38 in two paths, each path cauterizing the adjacent tissue resulting in cauterized tissue ends 38a,38b. Electrical energy flows from the cutting edge 106 to each of the first and second electrodes 602,604 of the second member 104. This dual flow of electrical energy assists the mechanical cutting of the cutting edge 106 and provides a better cauterization of the tissue ends 38a,38b adjacent to the cutting edge 106. A further advantage of this arrangement over that shown in FIG. 11A is that if the instrument is accidentally energized without tissue 38 being present in between the cutting edge 106 and anvil surface 108, the instrument will not short because the anvil surface is non-conducting. This is not the case in the bipolar arrangement as shown in FIG. 11A.

FIG. 11D shows another bipolar arrangement comprising a first and second cutting edge 106a,106b, each of which serves as an electrode of opposite polarities. Disposed between the first and second cutting edges 106a,106b is a non-conductive insulating layer 606 for electrically isolating the first cutting edge 106a from the second cutting edge 106b. The insulating layer 606 is preferably a non-conductive material such as aluminum oxide. The second member 104 and the anvil surface 108 are made of a durable non-conductive material, preferably aluminum oxide which is durable enough to withstand the pressure applied by the cutting edges 106a,106b. As shown in FIG. 12D, this arrangement results in mechanical cutting from two cutting edges, cauterization which is isolated in the region of cutting, as well as preventing accidental shorting of the instrument as discussed above.

FIGS. 11E and 11F illustrate two variations of a bipolar configuration of the present invention whereby the cutting edge 106 and anvil surface 108 are made of a non-conductive insulating material durable enough to withstand the pressures from the mechanical cutting, such as aluminum oxide. Additionally, sandwiched on each side of the first and second members 102,104 are electrodes 608,610, 612,614. The variations differing only as to how the polarities of the electrodes are arranged.

FIGS. 11E and 12E show one such version. The cutting edge 106 is non-conductive and disposed between electrodes 608 and 610. Likewise, the anvil surface is non-conductive and is disposed between electrodes 612 and 614. The electrodes 608, 610 of the first member 102 oppose the electrodes 612,614 of the second member 104. The polarities of the electrodes are arranged such that the polarities of the electrodes 608,610 of the first member 102 are the same. The polarities of the electrodes 612,614 of the second member 104 are also the same but opposite to the polarities of the electrodes 610,612 of the first member 102. As shown in FIG. 12E, the cutting edge 106 offers only mechanical cutting, cauterization of the cut ends 38a,38b of the tissue 38 is supplied by the adjacent electrodes 608,610,612,614 on both sides of the cutting edge 106. Like the configurations shown in FIGS. 11C and 11D, there is no possibility of accidental shorting with this configuration.

FIGS. 11F and 12F show a similar arrangement where the cutting edge 106 and anvil surface 108 are non-conductive. Like the configuration shown in FIGS. 11E and 12E, the cutting edge 106 is also disposed between electrodes 608 and 610 and the anvil surface is disposed between its own electrodes 612 and 614. Again, the electrodes 608, 610 of the first member 102 oppose the electrodes 612,614 of the second member 104. However, in this configuration the polarities of electrodes 608, 610 of the first member 102 are opposite to each other, as are the polarities of the electrodes 612,614 of the second member 104. The electrodes are arranged such that each electrode opposes an electrode of the opposite polarity. As shown in FIG. 12F, the cutting edge 106 offers only mechanical cutting, cauterization of the cut ends 38a,38b of the tissue 38 is supplied by the adjacent electrodes on both sides of the cutting edge 106. Like the configurations shown in FIGS. 11C, 11D, and 11E there is no possibility of shorting with this configuration.

Figure 11H:
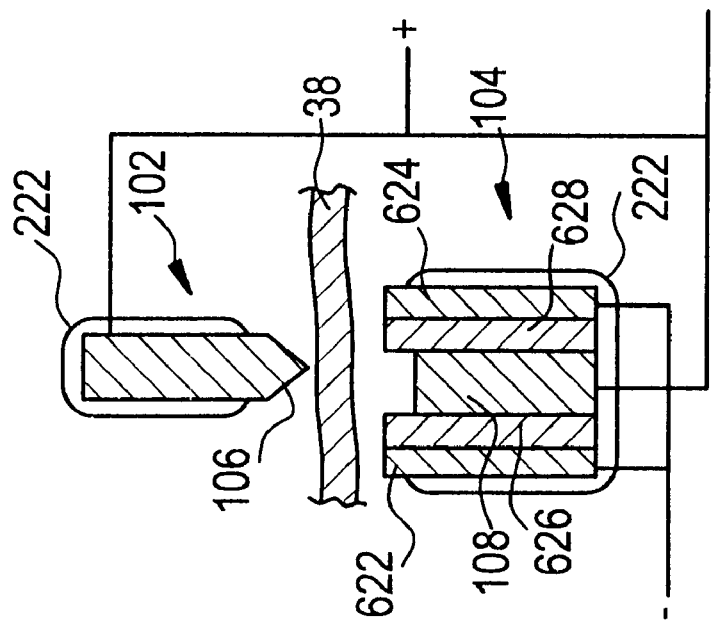
Figure 11G:
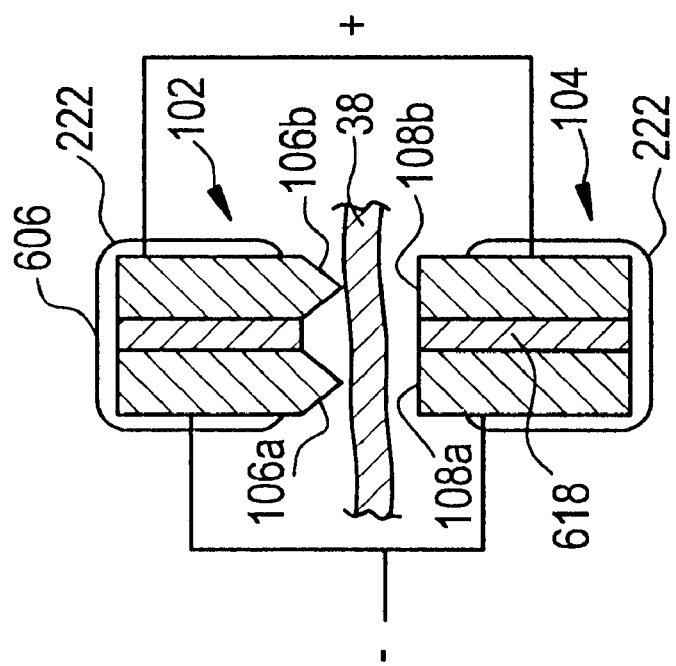

FIG. 11G shows a bipolar arrangement comprising a first member 102 having a first and second cutting edge 106a, 106b each of which serves as an electrode of opposite polarity. Disposed between the first and second cutting edges 106a,106b is a non-conductive material 606 for electrically isolating the first cutting edge 106a from the second cutting edge 106b. The non-conductive material is preferably a layer of insulating material such as aluminum oxide.

The second member 104 has first and second anvil surfaces 108a,108b each of which serves as an electrode of opposite polarity. Disposed between the first and second anvil surfaces 108a,108b is a non-conductive material 618 for electrically isolating the first anvil surface 108a from the second anvil surface 108b. The non-conductive material is preferably a layer of insulating material such as aluminum oxide. The electrodes are arranged such that pairs of electrodes with like polarities oppose each other.

Figure 12G:
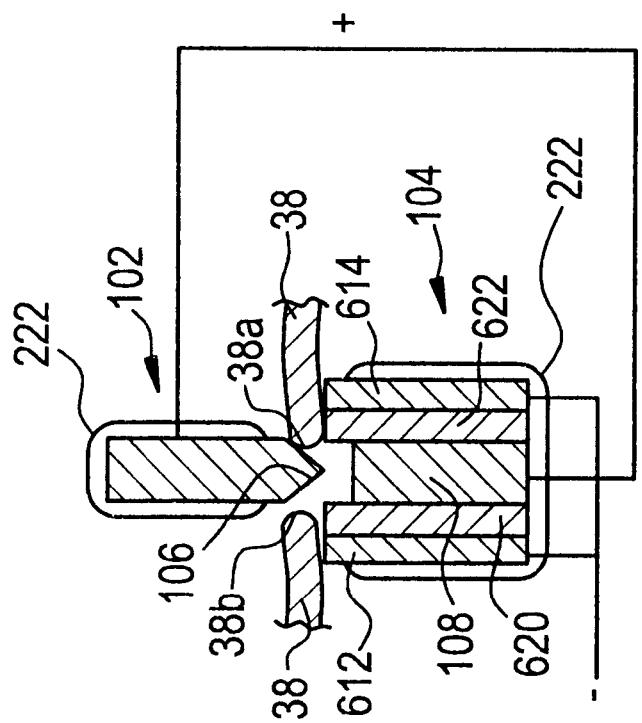

Specifically, as shown in FIG. 11G, cutting edge 106a and anvil surface 108a form a first pair of opposing electrodes having the same polarity. Similarly, cutting edge 106b and anvil surface 108b form a second pair of electrodes having the same polarity, but opposite to the polarity of the first pair of electrodes. As shown in FIG. 12G, this arrangement results in mechanical cutting of the cutting edges 106a,106b against the anvil surfaces 108a,108b as well as bipolar cauterization due to the electrode arrangement.

Like, the arrangements discussed previously, the arrangement shown in FIG. 11G prevents accidental shorting of the electrodes, however it is accomplished in a different manner. Instead of preventing accidental shorting by providing an insulating anvil surface or cutting edge, the bipolar electrode arrangement of FIG. 11G prevents accidental shorting by having opposing electrodes with the same polarity. However, bipolar cauterization is achieved due to the electrode pairs being opposite in polarity from each other.

FIG. 11H shows a bipolar arrangement comprising a first member 102 having a cutting edge 106 which serves as an electrode having a polarity. The second member 104 has an anvil surface 108 opposing the cutting edge 106 and serving as an electrode of the same polarity as the cutting edge 106. The cutting edge 106 and anvil surface 108 form a first pair of electrodes having the same polarity.

The second member 104 also has a second pair of electrodes 622,624 having the same polarity as each other, but opposite in polarity to the first pair of electrodes comprising the cutting edge 106 and anvil surface 108. Disposed between the second pair of electrodes 622,624 and the anvil surface 108 are non-conductive materials 626,628 for electrically isolating the second pair of electrodes 622,624 from each other and from the anvil surface 108. The non-conductive material is preferably a layer of an insulating material such as aluminum oxide. The electrodes are arranged such that the first pair of electrodes oppose each other and the second pair of electrodes diagonally oppose the cutting edge 106.

Figure 12H:
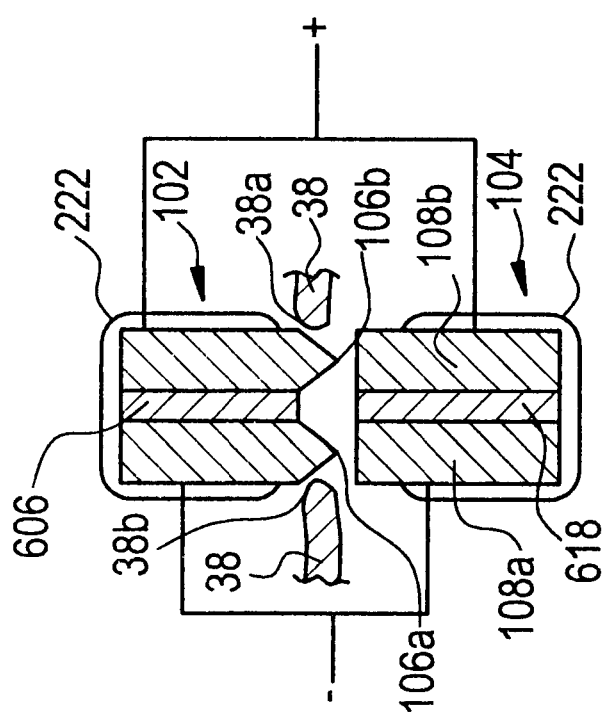

As shown in FIG. 12H, this arrangement results in mechanical cutting of the cutting edge 106 against the anvil surfaces 108 as well as bipolar cauterization due to the electrode arrangement. Like, the electrode arrangement of FIG. 11G, the arrangement shown in FIG. 11H prevents accidental shorting of the electrodes by having opposing electrodes with the same polarity. However, in the arrangement of FIG. 11H only the first pair of opposing electrodes contact, namely the cutting edge 106 and anvil surface 108. The second pair of electrodes having the same polarity do not contact but provide bipolar cauterization due to their opposition to the cutting edge 106 which is of the opposite polarity.

Referring now in detail to FIGS. 5, 5A, and 6, in which a second embodiment of the present invention is illustrated for use in open surgical procedures. The embodiment illustrated in FIGS. 5, 5A, and 6 in which all components similar to or identical with those in FIGS. 3 and 4 are designated with the same reference numerals, is merely modified with regard to the previous embodiment, in that the means to maintain the cutting edge 106 and the anvil surface 108 parallel comprises a different mechanical linkage 110a from that of the previous embodiment 100.

Like the previous embodiment, the present embodiment can be configured with any desired profile anvil surface 108 and opposing cutting edge 106, in a monopolar version, in any of the bipolar versions shown in FIGS. 11A, and 11C–11H, with the anvil surface configured with a recessed portion 109a as shown in FIGS. 10A and 10B, or in reusable or disposable versions.

Referring back to FIGS. 5, 5A, and 6, the mechanical linkage 110a comprises a first parallel linkage 502 and a second parallel linkage 504. Each of the first and second parallel linkages 502,504 comprises a first link member 506,510 and a second link member 508,512. Each link member 506,508,510,512 being of equal length and having a distal end 506a, 508a, 510a, 512a and a proximal end 506b, 508b, 510b, 512b.

The second link members 508,512 are pivotally connected at their distal ends 508a,512a, to the first and second members 102,104 respectively at pivot points 516 and 520 respectively. The proximal ends 508b,512b of the second link members 508,512 are connected to, and may be integral with, the distal ends 206,212 of the first and second handle levers 202,208 respectively. As discussed previously, the pivot points are typically pins, screws or rivets and can be fabricated from a number of materials.

The first link members 506,510 are pivotally connected at their distal ends 506a,510a, to the first and second members 102,104 respectively at pivot points 514 and 518 respectively. The proximal ends 506b,510b of the first link members 506,510 are pivotally connected to the second link members 512,508 respectively at pivot points 524 and 526 respectively.

The first and second members 102,104 preferably being devised at pivot points 514,516,518, and 520 to accept their respective link members.

The first and second link members 506,508 of the first parallel linkage 502 are arranged such that they are parallel to each other. Likewise, he first and second link members 510,512 of the second parallel linkage 504 are arranged such that they are parallel to each other. A perpendicular link member 522 is pivotally connected at each of its ends at pivot points 524 and 526 perpendicular to the line of movement of parallel jaw members 102,104. The perpendicular link member 522 maintains the parallel relationship of the first and second parallel linkages 502,504.

As can be seen in FIG. 5A, first link member 510 and second link member 512 of the second parallel linkage 504 are devised to provide interior voids 510c,512c for slidably accepting the first and second link members 506,508 of the first parallel linkage 502 within the voids 510c,512c.

The instrument as shown in FIGS. 5, 5A, and 6 is actuated in the same way as in the previous embodiment, buy inserting fingers into the finger loops 214 and 216 and squeezing the fingers together. When the first and second handle levers 202,208 are bought together by the squeezing, the first and second parallel linkages 502,504 maintain their parallel relationship causing the first and second jaw members 102,104 to move toward each other until the cutting edge 106 contacts the anvil surface 108. During the movement of the jaw members 102,104 the cutting edge 106 is maintained parallel to the anvil surface 108. Reversal of the above procedure opens the jaw members 102,104 while maintaining the cutting edge 106 parallel to the anvil surface 108.

The instrument of the present embodiment is energized in a bipolar configuration as was previously discussed in relation to the first embodiment. However, the first and second handle levers 202,208 supply electrical energy of different polarities directly to the first and second members 102,104.

The two electrical paths are isolated by fabricating the first link elements 506,510 and the perpendicular link member 522 from non-conducting material, such as a high strength polymer or ceramic. Additionally the second link member 508 of the first parallel linkage 502 must be isolated from the second link member 512 of the second parallel linkage 504 at all points of sliding contact between them. Preferably the isolation is accomplished by disposing insulating coatings 508c,508d on each side of second link member 508. Preferably, the insulating coating is aluminum oxide, plasma deposited at a thickness of between 0.005 and 0.007 inches thick.

Lastly, the present embodiment is insulated to prevent electrical shock to the user. This is accomplished in the same manner as previously discussed with regard to the previous embodiment.

Referring now in detail to FIGS. 7, 7A, and 8, in which a third embodiment of the present invention is illustrated for use in open surgical procedures. The embodiment illustrated in FIGS. 7, 7A, and 8 in which all components similar to or identical with those in FIGS. 5, 5A, and 6 are designated with the same reference numerals, is merely modified with regard to the previous embodiment, in that the means to maintain the cutting edge 106 and the anvil surface 108 parallel comprises a different mechanical linkage 110b from that of the previous embodiment 100a. Mechanical linkage 110b being a single jaw movement version of mechanical linkage 110a in which both the first and second members 102,104 move relative to each other.

Like the previous embodiment, the present embodiment can be configured with any desired profile anvil surface 108 and opposing cutting edge 106, in a monopolar version, in any of the bipolar versions shown in FIGS. 11A–11H, with the anvil surface configured with a recessed portion 109a as shown in FIGS. 10A and 10B, or in reusable or disposable versions.

Referring back to FIGS. 7, 7A, and 8, the mechanical linkage 110b comprises a parallel linkage 702. The parallel linkage 702 comprises a first link member 704 and a second link member 706. The link members 704,706 are of equal length and have a distal end 704a,706a and a proximal end 704b,706b.

A rigid link 708 has a distal end 708a, a proximal end 708b, and an upturned portion 708c between the distal end 708a and proximal end 708b. The distal end 708a of the rigid link 708 is connected to, and preferably an integral part of, the second member 104. The proximal end 708b of the rigid link 708 is connected to, and preferably an integral part of, the distal end 212 of the second handle lever 208.

The second link member 706 of the parallel linkage 702 is pivotally connected at its distal end 706a to the first member 102 at pivot point 712. The proximal end 706b of the second link member 706 is connected to, and preferably an integral part of, the distal end 206 of the first handle lever 202. Additionally the proximal end 706b of the second link member 706 is pivotally connected to the rigid member 708 at pivot point 716. As discussed previously, the pivot points are typically pins, screws or rivets and can be fabricated from a number of materials.

The first link member 704 of the parallel linkage 702 is pivotally connected at its distal end 704a to the first member 102 at pivot point 710. The proximal end 704b of the first link member 704 is pivotally connected to the rigid members 708 at pivot point 714. Pivot points 714 and 716 are disposed within the upturned portion 708c of the rigid member 708.

The first member 102 preferably being clevised at pivot points 710 and 712 to accept their respective link members.

The first and second link members 704,706 of the parallel linkage 702 are arranged such that they are parallel to each other. The parallel arrangement of link members 702,704 is maintained throughout the link members 702,704 range of motion.

As can be seen in FIG. 7A, the rigid member 708 is devised to provide an interior void 708d for slidably accepting the first and second link members 704,706 of the parallel linkage 702 within the void 708d.

The instrument as shown in FIGS. 7, 7A, and 8 is actuated in the same way as in the previous embodiment, by inserting fingers into the finger loops 214 and 216 and squeezing the fingers together. When the first and second handle levers 202,208 are bought together by the squeezing, the first parallel linkage 702 maintains its parallel relationship causing the first and second jaw members 102,104 to move toward each other until the cutting edge 106 contacts the anvil surface 108. During the movement of the jaw members 102,104 the cutting edge 106 is maintained parallel to the anvil surface 108. Reversal of the above procedure opens the jaw members 102,104 while maintaining the cutting edge 106 parallel to the anvil surface 108.

The instrument of the present embodiment is energized in a bipolar configuration as was previously discussed in relation to the previous embodiment with the first and second handle levers 202,208 supplying electrical energy of different polarities directly to the first and second members 102, 104.

The two electrical paths are isolated by fabricating the first link element 704 from non-conducting material such as a high strength polymer or ceramic. Additionally the rigid member 708 must be isolated from the second link member 706 of the parallel linkage 702 at all points of sliding contact between them and at pivot point 716. Preferably the isolation is accomplished by disposing insulating coatings 706c,706d on each side of second link member 706 and the pin, rivet, or screw at pivot point 716. Preferably, the insulating coating is aluminum oxide, plasma deposited at a thickness of between 0.005 and 0.007 inches thick. As discussed previously, the pin, rivet, or screw at pivot point 716 can be alternatively fabricated entirely from an insulating material.

Lastly, the present embodiment is insulated to prevent electrical shock to the user. This is accomplished in the same manner as previously discussed with regard to the two previous embodiments.

Referring now to FIG. 13, the present invention, generally referred to by reference numeral 900, is shown configured for endoscopic procedures. The endoscopic electrosurgical cutting instrument 900 includes a first member 902 and a second member 904. The first member 902 has at least one cutting edge 906. The second member 904 has an anvil surface 908 opposing the cutting edge 906 of the first member 902. In the preferred embodiment the first member 902 and second member 904 move relative to each other. However, one of the members can also be made to move while the other member is stationary. The anvil surface 908 can have a recessed portion 109*a* as shown in FIGS. 5A and 5B as discussed in relation to the open surgery version 100 of the present invention.

Figure 15:
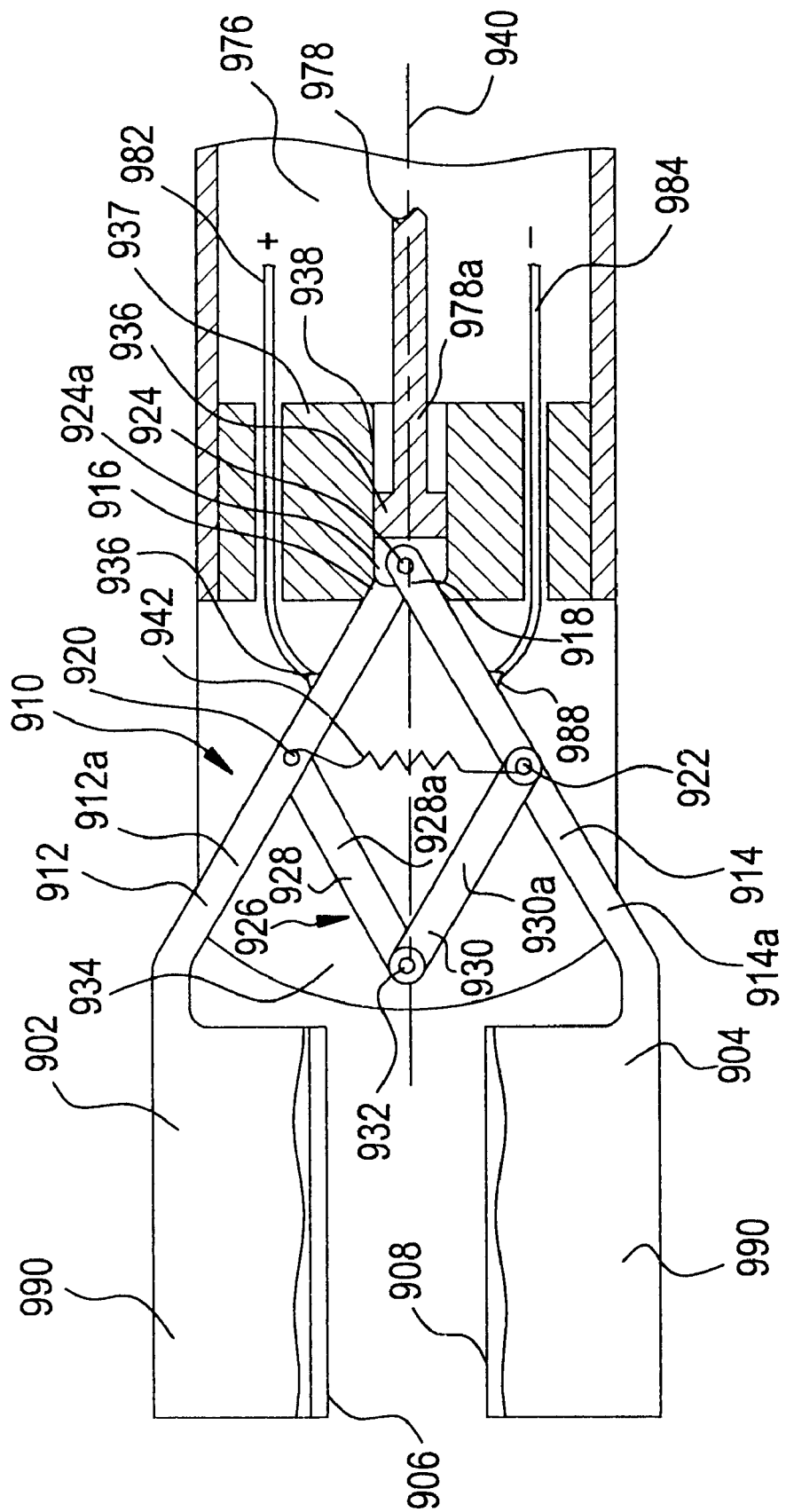
FIG. 15 illustrates an enlarged partial sectional view of the distal end of the present invention as shown in FIG. 14.

Referring to FIG. 13, a means for maintaining the cutting edge 906 parallel with the anvil surface 908 in which both the first member 902 and second member 904 move relative to each other between an open and closed position is supplied by a mechanical linkage generally referred to as reference numeral 910 in FIG. 15. The mechanical linkage 910, of which any straight-line or parallel motion linkage can be employed, has a first rigid member 912, connected, and preferably integral with, the first member 902. Likewise, the mechanical linkage 910 has a second rigid member 914, connected to, and preferably integral with, the second member 904. The first rigid member 912, and second rigid member 914 each have a cantilevered end 916,918 respectively and a pivot point, 920,922 located at a point halfway along its length. The cantilevered end 916 of the first rigid member 912 intersects the cantilevered end 918 of the second rigid member 914 at pivot point 924. A first linkage 926 is provided which includes first and second link elements 928,930. The link elements 928,930 are of equal length to each other and equal to the distance between the pivot points 924 and 920 or 922. Each link element having a first and second pivot point, the first pivot points being pivotally connected together at 932 which is fixed to the instrument at its distal end 934, meaning that point 934 is restrained from moving relative to the other pivot points of the linkage. The second pivot points coincide with pivot points 920 and 922 of the first and second rigid members 912, 914, and are pivotally connected therewith.

A slide 936 is provided which is pivotally connected to the cantilevered ends 916,918 of the first and second rigid members 912,914. A means to limit the motion of the slide along an axis 940 which is defined by a line intersecting pivot points 924 and 932 is provided by a plug 937 having a conduit 938 in which the slide 936 is slidably disposed. A spring 942 is disposed between pivot points 920 and 922 to bias the first member 902 and second member 904 in their closed position.

As discussed previously with regard to the open surgery version of the present invention 100, all pivoting points used on the instrument are accomplished by means well known in the art, such as with pins, screws, or rivets. As discussed previously, the pins, screws or rivets can be fabricated from a number of materials.

Actuating means, referred to generally as 950 in FIG. 13, is supplied for opening and closing the first and second members 902,904 between their open and closed positions in which a first handle lever 952 having a proximal end 954 and a distal end 956 is provided. Also provided, is a second handle lever 958 having a proximal end 960 and a distal end 962. The second handle lever 958 pivotally connects to the first handle lever 952 about pivot point 964. Finger loops 966 and 968 are disposed on the proximal ends 954,960 of the first and second handle levers 952,958 respectively.

An elongated tube 970 having a distal end 972, a proximal end 974, and a lumen 976 is provided. The proximal end 974 of the elongated tube 970 is fixed to the proximal end 956 of the first handle lever 952. A means for connecting the second handle lever 958 to the slide 936 is provided by a wire member 978 disposed in the lumen 976 of the elongated tube 970. The wire member having a proximal end 978*b* and a distal end 978*a,* the proximal end 978*b* being pivotally connected to the distal end 962 of the second handle lever 958 and the distal end 978*a* being connected to, and preferably integral with, the slide as shown in FIG. 15.

To actuate the instrument, a user inserts his or her fingers into finger loops 966 and 968 and either squeezes them together or spreads them apart which causes the second handle lever 958 to pivot about pivot point 964 which causes the wire member 978 to push or pull the slide 936 in the conduit 938, which in turn actuates the first and second members 902,904 between their open and closed positions.

Starting from an open position, as shown in FIG. 15, the user would squeeze his fingers together which will pivot the second handle lever 958 relative to the first handle lever 952, which will pull on the wire member 978 and cause the wire member 978 to pull the slide 936 within the conduit 938. The cantilevered ends 916,918 of the first and second rigid members 912,914 will translate with the slide 936. Since the mechanical linkage 910 is fixed at point 932, the first and second rigid members 912,914 will also rotate about point 924, however their rotation is constrained by the first linkage 926. The resulting motion will be that of parallel or straight-line motion at the points on the first and second rigid members 912,914 adjacent to the first and second members 902,904. The first and second members 902,904 being connected therewith are constrained to move parallel to each other and toward each other until the cutting edge 906 contacts the anvil surface 908.

To open the first and second members 902,904 the above described motion is reversed, however, in this motion enough force must be exerted by the user to overcome the biasing force of the spring 942 which biases the first and second members 902,904 in their closed position. Since the distal end 934 of the instrument 900 must be passed through a trocar tube (not shown) it is important that the first and second members 902,904 be biased in their closed position, since in such a position their cross-sectional profile is smallest.

Electrical energy is supplied to the electrodes of the first and second members 902,904 by a electrosurgical generator (not shown) via a power cord 980 fixed at one end to the distal end 956 of the first handle lever 952 and at the other end (not shown) to the electrosurgical generator. The power cord 980 contains two leads, one lead of a certain polarity, the other of the opposite polarity. Insulated wires 982,984 are disposed in the lumen 976 of the elongated tube 970 for the purpose of carrying the electrical energy from the power cord 980 to the electrodes of the first and second members 902,904. The proximal ends (not shown) of the insulated wires 982,984 are electrically connected to the leads of the power cord 980. The distal ends 986,988 of the insulated wires 982,984 are electrically connected to the first and second rigid members 912,914, preferably by a soldered joint. The first and second rigid members 912,914, as well as the electrodes of the first and second members 902,904 are made of a conductive material, preferably stainless steel. When called for by the user (usually through a foot switch electrically connected to the electrosurgical generator), the generator supplies electrical energy through each lead of the power cord 980. Each lead of the power cord 980 connects to one of the insulated wires 982,984, which supplies the electrical energy to the first and second rigid members 912,914, and ultimately to the first and second members 902,904 connected therewith. The polarity of the leads of the power cord 980 is matched with the polarity requirements for the first and second members 902,904.

To isolate the two electrical paths, an isolating means is provided to electrically isolate the first member 902 from the second member 904. In the preferred embodiment, as shown in FIG. 15, the isolating means is accomplished by disposing insulating layers of aluminum oxide to link elements 928 and 930, referred to as 928a, 930a respectively. A layer of aluminum oxide is also disposed to the first and second rigid members 912,914, referred to as 912a,914a, to both sides of the slide 924 where it contacts the first and second rigid members 912,914, referred to as 924a and 924b (not shown), and at all pivot points as an aluminum oxide coating, referred to as 920a, 922a, 924a, and 932a. Preferably the plug 937 is also fabricated from a non-conductive material such as aluminum oxide.

Alternatively, link elements 928,930 of linkage 926 are fabricated from an insulating material such as a high strength polymer or a ceramic. Therefore the need for insulating coatings 928a and 930a is eliminated. The pivot pins at pivot points 920, 922, 924, and 932 can also be fabricated from an insulating material as previously discussed.

Lastly, an insulating means is provided for preventing electrical conduction from portions of the instrument other than the electrodes. Preferably, the insulating means comprises a nylon coating 990 secured to all portions of the instrument where electrical conduction is not wanted. This most likely includes all portions of the instrument except the cutting edge 906, anvil surface 908, and portions of the electrodes closest to where they meet when the first and second members 902,904 when in their closed position (if the electrodes are not the cutting edge 906 or the anvil surface 908). This insulating coating 990 serves to protect the user from electrical shock and burning, and also the patient from electrical shock and burning in areas other than those intended.

The endoscopic version of the present invention can also be configured in a monopolar configuration, as discussed above and shown in FIGS. 11B and 12B, where only one polarity is provided, the other polarity being provided by the patient's body, by which current flows back to the electrosurgical generator. In this configuration, both the cutting edge 906 and the anvil surface 908 are electrodes of the same polarity, a grounding plate (shown schematically as ground 600) attached to the patient and to the electrosurgical generator allows current to flow from the instrument through the patient and back to the generator. Electrical current is supplied to the instrument in a similar fashion, except that only one insulated wire is necessary. In this configuration an isolating means is not necessary since there is only one current path through the instrument.

The endoscopic electrosurgical cutting instrument 900 can be configured in any of the bipolar configurations as discussed previously with regard to the open surgery versions 100, 500, and 700 of the present invention. In fact, all of the bipolar configurations, as discussed above and shown in FIGS. 11A, and 11C–11H and 12A, and 12C–12H are equally applicable to the endoscopic version 900 as shown in FIGS. 13, 14, and 15.

It should also be noted that the endoscopic embodiment of the present invention can be modified to be utilized in open surgical procedures. This can be accomplished by shortening the elongated tube 970, increasing the size of the first and second members 102,104, and by providing "in-line" handle levers 952,958, of which surgeons performing open surgery are more accustomed.

Figure 16:
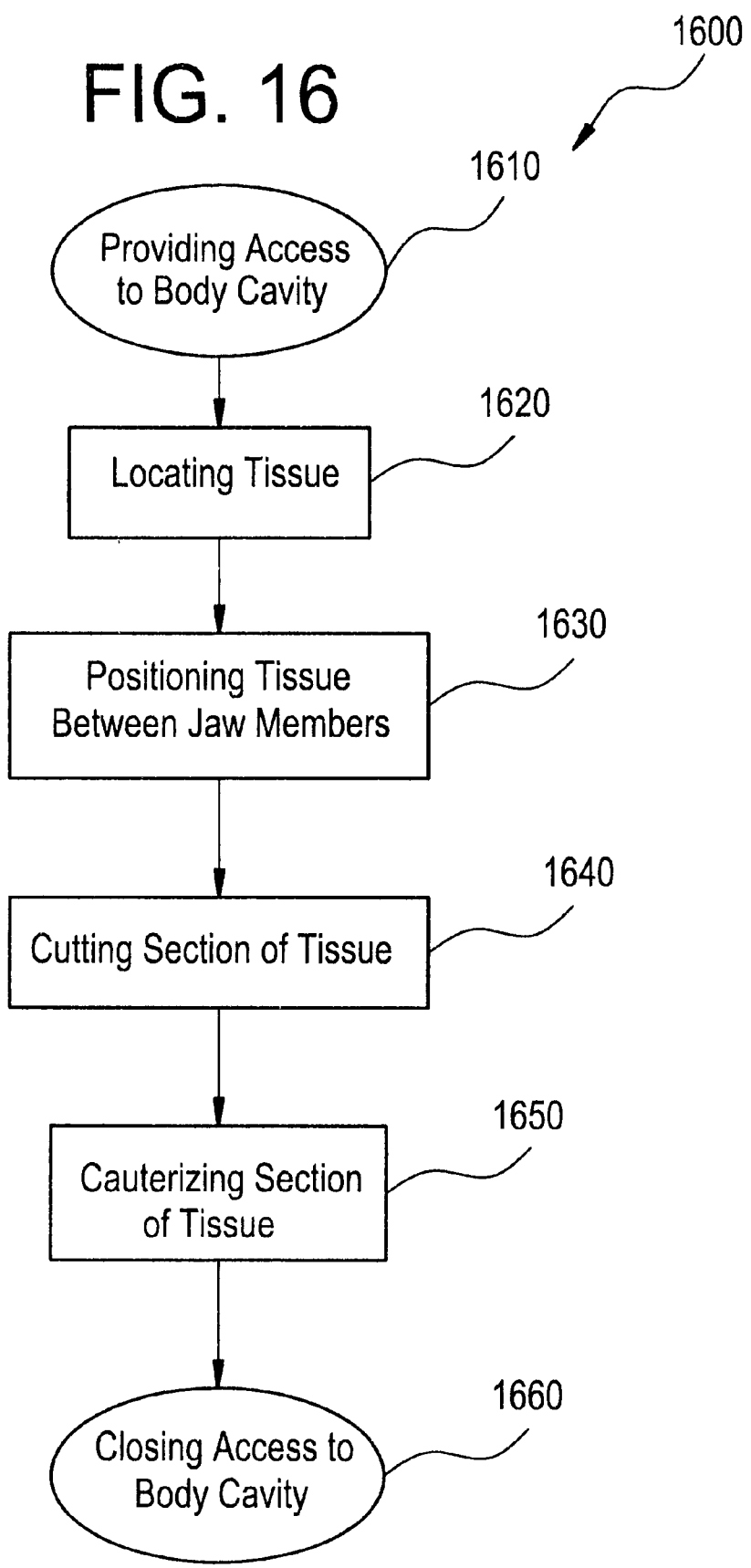
FIG. 16 illustrates the steps of a method for using the present invention as shown in any one of the embodiments illustrated in FIGS. 3, 5, or 7.

Referring now to FIG. 16, the steps outlining a method for using an open surgery version of the present invention are illustrated and referred to generally by reference numeral 1600. Access is first provided in step 1610 to the tissue (or vessel) 38 to be cauterized and cut by exposing the interior of a body cavity. This is typically achieved by making a large incision through the skin and body wall. The tissue 38 to be cauterized and cut is then located in step 1620. The located tissue 38 is positioned between the first and second members of the instrument after actuating the instrument in step 1630 into an open position.

A section of tissue 38 is then mechanically cut in step 1640 by the force of the cutting edge(s) 106 against the anvil surface 108 when the instrument is actuated into a closed position. Alternatively, if the anvil surface 108 is configured with a recessed portion 109a, then the mechanical cutting step (1640) is achieved by the force of the cutting edge against the edges 109b,109c of the recessed portion 109a in addition to the cutting edge 106.

A section of tissue 38 is simultaneously cauterized in step 1650 by energizing the instrument with RF energy supplied by an electrosurgical generator 123 resulting in cauterized tissue ends 38a,38b. The cutting step (1640) and cauterizing step (1650) can be carried out separately as described above, however they are preferably done simultaneously whereby the surgeon energizes the instrument while actuating the instrument into a closed position. Furthermore, the instrument can be energized in either a monopolar or bipolar fashion.

Lastly, the access provided in step 1610 is closed in step 1660 by any standard means known in the surgical arts.

Figure 17:
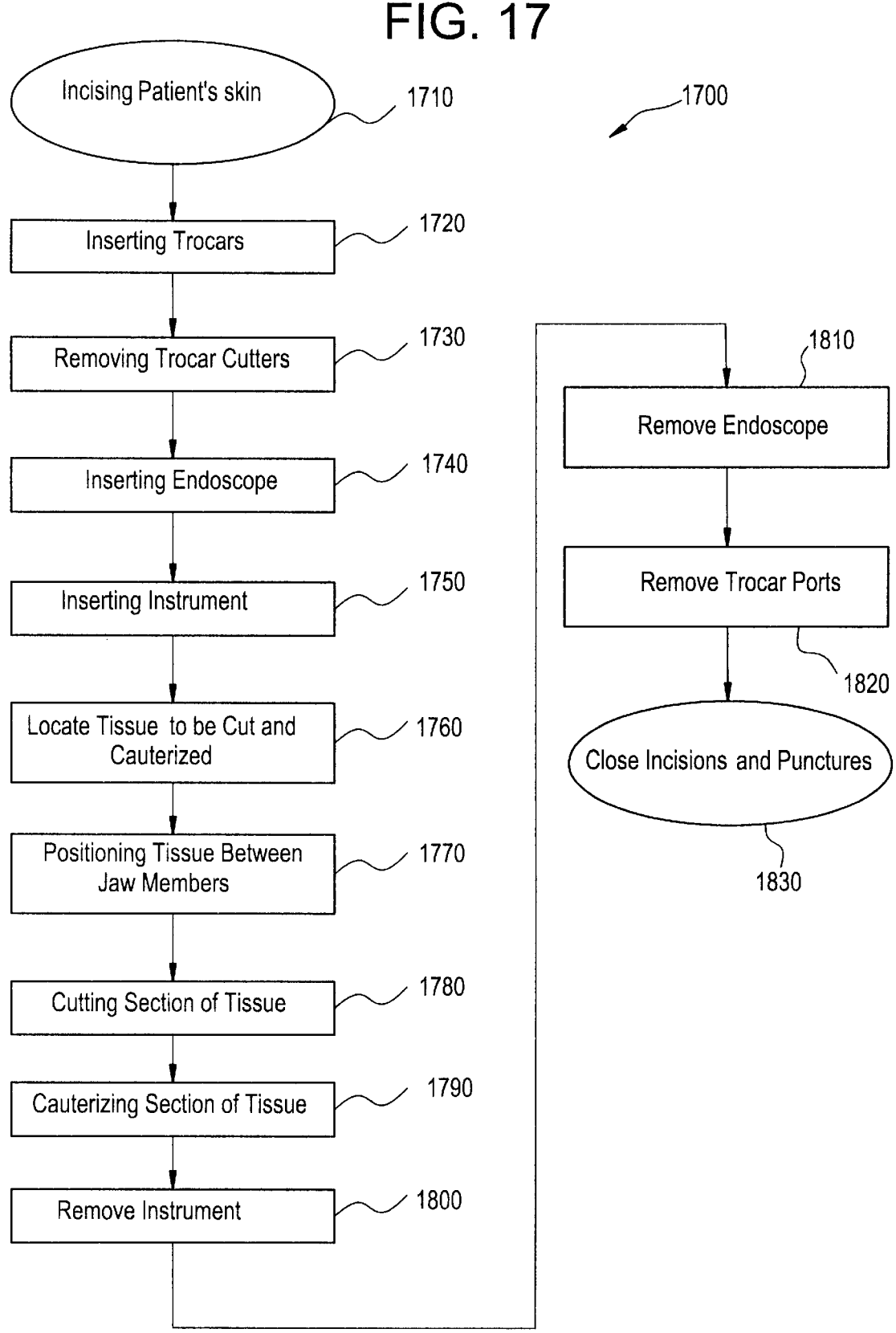
FIG. 17 illustrates the steps of a method for using the present invention as shown in FIG. 13.

Referring now to FIG. 17, the steps outlining a method for using an endoscopic version of the present invention are illustrated and referred to generally by reference numeral 1700. Incisions are made through the patient's skin in step 1710 for facilitating the entry of trocars (not shown). Each trocar comprises a cutter and a port. At least two trocars are inserted in step 1720 through the body wall by puncturing the body wall with the trocar cutter to provide access to the tissue (or vessel) to be cauterized and cut in the body cavity. The trocar cutters are removed in step 1730 leaving the trocar ports in place thus providing access to the body cavity. An endoscope is inserted in step 1740 into a trocar port thus providing a view of the body cavity on a monitor receiving video signals from the endoscope. An endoscopic version of the instrument of the present invention is then inserted into another trocar port in step 1750 whereby its distal end is inside the body cavity and viewable on the video monitor.

The tissue 38 to be cauterized and cut is then located in step 1760. The located tissue and/or vessel(s) 38 are positioned between the first and second members of the instrument in step 1770 after actuating the instrument into an open position.

A section of tissue 38 is mechanically cut in step 1780 by the force of the cutting edge(s) 106 against the anvil surface 108 when the instrument is actuated into a closed position. Alternatively, if the anvil surface 108 is configured with a recessed portion 109a, then the mechanical cutting step (1780) is achieved by the force of the cutting edge against the edges 109b,109c of the recessed portion 109a in addition to the cutting edge 106.

A section of tissue 38 is simultaneously cauterized in step 1790 by energizing the instrument with RF energy supplied by an electrosurgical generator 123 resulting in cauterized tissue ends 38a,38b. The cutting step (1780) and cauterizing step (1790) can be carried out separately as described above, however they are preferably done simultaneously whereby the surgeon energizes the instrument while actuating the instrument into a closed position. Furthermore, the instrument can be energized in either a monopolar or bipolar fashion.

The instrument and endoscope are then removed in steps 1800 and 1810 from the trocar ports. The trocar ports are also removed in step 1820. Lastly, the incisions and punctures are closed in step 1830 by any standard means known in the surgical arts.

From the foregoing, it becomes readily apparent to one skilled in the art that the novel electrosurgical cutting instruments are constituted of simpler parts to manufacture, offering an enhanced degree of product reliability through the simplicity in design and manufacture, which renders the instruments less expensive and highly economical in comparison with currently employed instruments.

Due to the inventive cutting arrangement, wherein the cutting edge and anvil surface are constrained to move substantially parallel to each other, the advantages offered by the inventive structure resides in:

(a) the inventive cutting structure results in the ability to simultaneously cut and cauterize a linear section of tissue;

(b) the simultaneous cutting and cauterization of tissue results in improved coagulation of blood and cauterization of tissue;

(c) the ability to simultaneously cut and cauterize linear sections of tissue provides for an instrument which is uniquely adapted for cutting and cauterizing large vessels;

(d) the ability to simultaneously cut and cauterize linear sections of tissue provides for an instrument which is uniquely adapted for simultaneously cutting and cauterizing a group of vessels;

(e) the cutting action of the inventive instrument reduces the amount of trauma to tissue during cutting as compared with the instruments of the prior art due to a slicing action which replaces the shearing associated with the instruments of the prior art;

(f) the inventive cutting structure results in an instrument wherein the cutting edge is less prone to wear; and (g) the production costs of the inventive instruments is considerably reduced due to the elimination of conventional rotating scissor blades which require complex surface contours, strict dimensional tolerances, and precise blade adjustment.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A scissorlike electrosurgical cutting instrument comprising:

a first member having at least one cutting edge;

a second member having an anvil surface opposing the cutting edge;

means for maintaining the cutting edge substantially parallel to the anvil surface in which at least one of the first and second members moves relative to the other member between an open and closed position such that the cutting edge comes into substantial contact with the anvil surface when the members are in their closed position;

at least one electrode disposed on or integral with the first member and at least one other electrode disposed on or integral with the second member, at least two of the electrodes being of opposite polarity for providing electrical energy for cauterization of tissue;

isolating means for electrically isolating the first member from the second member; and scissorlike actuation means for moving the first and second members between the open and closed positions.

2. The instrument as claimed in claim 1, wherein:

the cutting edge comprises the at least one electrode of the first member; and the at least one electrode of the second member comprises two electrodes of the same polarity, but of opposite polarity to that of the cutting edge, the anvil surface being a non-conductive material disposed between the two electrodes of the second member for electrically isolating one of the two electrodes of the second member from the other.

3. The instrument as claimed in claim 2, wherein the non-conductive material is aluminum oxide.

4. The instrument as claimed in claim 2, wherein the first and second members move relative to each other.

5. The instrument as claimed in claim 2, wherein the anvil surface further having a recessed portion for acceptance of the cutting edge when the first and second members are in their closed position.

6. The instrument as claimed in claim 2, further comprising means to bias the first and second members in one of their open or closed positions.

7. The instrument as claimed in claim 2, wherein the instrument is shaped, sized, and configured to be suitable for open surgical procedures.

8. The instrument as claimed in claim 7, wherein the means for maintaining the cutting edge parallel to the anvil surface comprises a mechanical linkage.

9. The instrument as claimed in claim 8, wherein the mechanical linkage comprises:

a first rigid member extending from the first member, the first rigid member having a cantilevered end;

a second rigid member extending from the second member, equal in length to the first rigid member and parallel to the first rigid member, the second rigid member having a cantilevered end opposing the cantilevered end of the first rigid member;

a first linkage comprising two link elements of equal length, each link element having a first and second pivot point, the link elements being pivotally connected at their first pivot points and pivotally connected to the cantilevered ends of the first and second rigid members at their second pivot points;

a second linkage comprising two link elements of equal length and of the same length as the link elements of the first linkage, each link element having a first and second pivot point, the link elements being pivotally connected at their first pivot points and pivotally connected to the cantilevered ends of the first and second rigid members at their second pivot points;

a third linkage comprising two link elements of equal length and of the same length as the link elements of the first and second linkages, each link element having a first and second pivot point, the link elements being pivotally connected at their first pivot points and pivotally connected to opposite points on the first and second rigid members at their second pivot points; and a fixed member pivotally connected to the first pivot point of the first linkage and slidably connected to the first pivot points of the second and third linkages such that rotation of the link elements of the first linkage causes the cutting edge and anvil surface of the first and second members to move parallel relative to each other.

10. The instrument as claimed in claim 9, wherein the actuation means comprises first and second conductive handle levers, each handle lever having a distal and proximal end, the distal ends of the handle levers being connected to the link elements of the first linkage wherein the handle levers pivot about the first pivot point of the first linkage.

11. The instrument as claimed in claim 10 further comprising:
  a finger loop disposed on each of the proximal ends of the handle levers for actuating the first and second members between their open and closed positions;
  a connector port disposed on each of the finger loops of the first and second handle levers for transferring electrical energy through the handle levers to the electrodes of the first and second members; and
  insulating means for preventing electrical conduction from portions of the instrument other than the electrodes.

12. The instrument as claimed in claim 11, wherein the insulating means is a nylon coating secured to portions of the instrument other than the electrodes and connector ports.

13. The instrument as claimed in claim 9, wherein the isolating means comprises a non-conductive material disposed on the link elements, rigid members, fixed member, and/or pivot points for electrically isolating the first member from the second member.

14. The instrument as claimed in claim 13, wherein the non-conductive material is a layer of aluminum oxide.

15. The instrument as claimed in claim 8, wherein the mechanical linkage comprises:
  a first parallel linkage comprising first and second link members, each link member being of equal length to each other and having a distal and proximal end, the distal ends of the link members being pivotally connected to the first member;
  a second parallel linkage comprising first and second link members, each link member being of equal length to each other and to the link members of the first parallel linkage, the first and second link members of the second parallel linkage further having a distal and proximal end, the distal ends of the link members being pivotally connected to the second member;
  a perpendicular link member pivotally connected at one end to the proximal ends of the first link member of the first parallel linkage and the second link member of the second parallel linkage, the perpendicular link member being pivotally connected at its other end to the proximal ends of the first link member of the second parallel linkage and the second link member of the first parallel linkage, such that the link members of the first parallel linkage and the link members of the second parallel linkage are in a parallel relationship to one another and wherein pivoting of the parallel linkages toward each other about the perpendicular link member causes the cutting edge and anvil surface to move parallel relative to each other.

16. The instrument as claimed in claim 5, wherein the actuation means comprises first and second handle levers, each handle lever having a distal and a proximal end, the distal end of the first handle lever being connected to the proximal end of the second link member of the first parallel linkage and the distal end of the second handle lever being connected to the proximal end of the second link member of the second parallel linkage such that pivoting of the proximal ends of the handle levers toward each other about the perpendicular link member causes the first and second parallel linkages to move towards each other.

17. The instrument as claimed in claim 16 further comprising:
  a finger loop disposed on each of the proximal ends of the handle levers for actuating the first and second members between their open and closed positions;
  a connector port disposed on each of the finger loops of the first and second handle levers for transferring electrical energy through the handle levers to the electrodes of the first and second members; and
  insulating means for preventing electrical conduction from portions of the instrument other than the electrodes.

18. The instrument as claimed in claim 17, wherein the insulating means is a nylon coating secured to portions of the instrument other than the electrodes and connector ports.

19. The instrument as claimed in claim 15, wherein the isolating means comprises fabrication of the first link elements and the perpendicular member from a non-conductive material, and disposing a non-conductive material to the second link member of the first parallel linkage on all points of electrical contact between the second link member of the first parallel linkage and the second link member of the second parallel linkage.

20. The instrument as claimed in claim 19, wherein the non-conductive material is a layer of aluminum oxide.

21. The instrument as claimed in claim 8, wherein the mechanical linkage comprises:
  a parallel linkage comprising first and second link members, each link member being of equal length to each other and having a distal and a proximal end, the distal ends of the first and second link members being pivotally connected to the first member about first and second pivot pins respectively; and
  a rigid link member having a distal end, a proximal end, and an upturned portion disposed between the distal and proximal ends, the distal end of the rigid link member being connected to the second member, the proximal ends of the first and second link members being pivotally connected to the rigid link member at the upturned portion about third and fourth pivot pins, wherein the third pivot pin pivotally connects the first link member to the rigid link member and the fourth pivot pin pivotally connects the second link member to the rigid link member, such that the first and second link members are in a parallel relationship to each other, and whereby pivoting of the parallel linkage towards the rigid link member about the fourth pivot pin causes the cutting edge to move parallel relative to the anvil surface.

22. The instrument as claimed in claim 21, wherein the actuation means comprises first and second handle levers, each handle lever having a distal and a proximal end, the distal end of the first handle lever being connected to the proximal end of the second link member of the parallel linkage and the distal end of the second handle lever being connected to the proximal end of the rigid link member such that pivoting of the proximal ends of the handle levers toward each other causes the parallel linkage to move towards the rigid link member.

23. The instrument as claimed in claim 22 further comprising:
- a finger loop disposed on each of the proximal ends of the handle levers for actuating the first and second members between their open and closed positions;
- a connector port disposed on each of the finger loops of the first and second handle levers for transferring electrical energy through the handle levers to the electrodes of the first and second members; and
- insulating means for preventing electrical conduction from portions of the instrument other than the electrodes.

24. The instrument as claimed in claim 23, wherein the insulating means is a nylon coating secured to portions of the instrument other than the electrodes and connector ports.

25. The instrument as claimed in claim 21, wherein the isolating means comprises fabrication of the first link member and the fourth pivot pin from a non-conductive material and disposing a layer of non-conductive material to the second link member on all points of electrical contact between the second link member and the rigid link member.

26. The instrument as claimed in claim 25, wherein the non-conductive material is aluminum oxide.

27. The instrument as claimed in claim 2, wherein the instrument is shaped, sized, and configured to be suitable for endoscopic surgical procedures.

28. The instrument as claimed in claim 27, wherein the means for maintaining the cutting edge parallel to the anvil surface comprises a mechanical linkage.

29. The instrument as claimed in claim 28, wherein the mechanical linkage comprises:
- a first rigid member extending from the first member, the first rigid member having a length, a cantilevered end, and a pivot point located halfway along its length;
- a second rigid member extending from the second member, equal in length to the first rigid member, the second rigid member having a cantilevered end intersecting the cantilevered end of the first rigid member, and a pivot point located halfway along its length;
- a first linkage comprising two link elements of equal length and half the length of the first and second rigid members, each link element having a first and second pivot point, the link elements being pivotally connected at their first pivot points, the first pivot points being fixed to the instrument, the second pivot points of the first and second link elements being pivotally connected to the pivot points of the first and second rigid members;
- a slide, pivotally connected to the cantilevered ends of the first and second rigid members; and
- means to limit the motion of the slide along an axis intersecting the cantilevered ends of the first and second rigid members and the fixed point such that movement of the slide along the axis causes the cutting edge and anvil surface of the first and second members to move parallel relative to each other.

30. The instrument as claimed in claim 29, further comprising an elongated tube having a distal end, a proximal end, and a lumen, and wherein the actuation means comprises:
- a first handle lever secured to the proximal end of the elongated tube;
- a second handle lever pivotally connected to the first handle lever;
- means for connecting the second handle lever to the slide of the mechanical linkage such that pivoting of the second handle lever relative to the first handle lever moves the slide along the axis and actuates the first and second members between their open and closed positions; and
- insulating means for preventing electrical conduction from portions of the instrument other than the electrodes.

31. The instrument as claimed in claim 30, wherein the means for connecting comprises a wire member disposed through the lumen of the elongated tube, the wire member having a proximal end and a distal end, the proximal end of the wire member being pivotally connected to the second handle lever, the distal end of the wire member being connected to the slide such that pivoting of the second handle lever relative to the first handle lever moves the slide along the axis and actuates the first and second members between their open and closed positions.

32. The instrument as claimed in claim 31, wherein the isolating means comprises a non-conductive material disposed on the link elements, rigid members, slide, and/or pivot points for electrically isolating the first member from the second member.

33. The instrument as claimed in claim 32, wherein the non-conductive material is a layer of aluminum oxide.

34. The instrument as claimed in claim 1, wherein:
- the anvil surface is non-conductive; and
- the first member having two cutting edges, the at least one electrode of the first member comprising two electrodes, each electrode corresponding to one of the two cutting edges, one electrode being of opposite polarity to the other, the first member further having a non-conductive insulating layer disposed between the two cutting edges for electrically isolating one cutting edge from the other.

35. The instrument as claimed in claim 34, wherein the non-conductive material is aluminum oxide.

36. The instrument as claimed in claim 34, wherein the first and second members move relative to each other.

37. The instrument as claimed in claim 34, further comprising means to bias the first and second members in one of their open or closed positions.

38. The instrument as claimed in claim 34, wherein the instrument is shaped, sized, and configured to be suitable for open surgical procedures.

39. The instrument as claimed in claim 38, wherein the means for maintaining the cutting edge parallel to the anvil surface comprises a mechanical linkage.

40. The instrument as claimed in claim 34, wherein the instrument is shaped, sized, and configured to be suitable for endoscopic surgical procedures.

41. The instrument as claimed in claim 40, wherein the means for maintaining the cutting edge parallel to the anvil surface comprises a mechanical linkage.

* * * * *